US012329808B2

(12) United States Patent
Guirakhoo et al.

(10) Patent No.: US 12,329,808 B2
(45) Date of Patent: *Jun. 17, 2025

(54) COMPOSITIONS AND METHODS FOR GENERATING AN IMMUNE RESPONSE TO TREAT OR PREVENT MALARIA

(71) Applicant: GeoVax, Inc., Smyrna, GA (US)

(72) Inventors: Farshad Guirakhoo, Atlanta, GA (US); Arban Domi, Atlanta, GA (US); Nathanael Paul McCurley, Decatur, GA (US)

(73) Assignee: GeoVax, Inc., Smyrna, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/394,580

(22) Filed: Dec. 22, 2023

(65) Prior Publication Data

US 2024/0398922 A1    Dec. 5, 2024

Related U.S. Application Data

(63) Continuation of application No. 17/726,254, filed on Apr. 21, 2022, now Pat. No. 11,857,611, which is a continuation of application No. 16/648,693, filed as application No. PCT/US2018/051652 on Sep. 19, 2018, now Pat. No. 11,311,612.

(60) Provisional application No. 62/560,405, filed on Sep. 19, 2017.

(51) Int. Cl.
| A61K 39/015 | (2006.01) |
| A61K 9/00 | (2006.01) |
| A61K 47/69 | (2017.01) |
| A61P 33/06 | (2006.01) |
| A61K 39/00 | (2006.01) |

(52) U.S. Cl.
CPC .......... *A61K 39/015* (2013.01); *A61K 9/0019* (2013.01); *A61K 47/6901* (2017.08); *A61P 33/06* (2018.01); *A61K 2039/5256* (2013.01); *A61K 2039/54* (2013.01)

(58) Field of Classification Search
CPC .... A61K 39/015; A61K 47/6901; A61P 33/06
See application file for complete search history.

(56) References Cited

U.S. PATENT DOCUMENTS

| 4,603,112 A | 7/1986 | Paoletti et al. |
| 4,722,848 A | 2/1988 | Paoletti et al. |
| 4,769,330 A | 9/1988 | Paoletti et al. |
| 5,445,953 A | 8/1995 | Dorner et al. |
| 6,103,244 A | 8/2000 | Dorner et al. |
| 6,440,422 B1 | 8/2002 | Sutter et al. |
| 6,696,281 B1 | 2/2004 | Chambers et al. |
| 6,998,252 B1 | 2/2006 | Moss et al. |
| 7,015,024 B1 | 3/2006 | Moss et al. |
| 7,045,136 B1 | 5/2006 | Moss et al. |
| 7,045,313 B1 | 5/2006 | Moss et al. |
| 7,550,147 B2 | 6/2009 | Howley et al. |
| 7,795,017 B2 | 9/2010 | Robinson et al. |
| 8,288,125 B2 | 10/2012 | Howley et al. |
| 8,309,326 B2 | 11/2012 | Howley et al. |
| 8,414,900 B2 | 4/2013 | Howley et al. |
| 8,435,543 B2 | 5/2013 | Howley et al. |
| 8,623,379 B2 | 1/2014 | Robinson et al. |
| 8,900,595 B2 | 12/2014 | Kawaoka et al. |
| 8,916,172 B2 | 12/2014 | Moss et al. |
| 9,133,478 B2 | 9/2015 | Moss et al. |
| 9,133,480 B2 | 9/2015 | Moss et al. |
| 9,453,239 B2 | 9/2016 | Moss et al. |
| 9,683,020 B2 | 6/2017 | Compans et al. |
| 9,879,231 B2 | 1/2018 | Moss et al. |
| 10,072,058 B2 | 9/2018 | Wang et al. |
| 11,311,612 B2 * | 4/2022 | Guirakhoo ........... A61K 9/0019 |
| 11,857,611 B2 * | 1/2024 | Guirakhoo .............. A61P 33/06 |
| 2003/0215794 A1 | 11/2003 | Kawaoka et al. |
| 2004/0109876 A1 | 6/2004 | Yamamoto et al. |
| 2005/0036985 A1 | 2/2005 | Ensoli |
| 2005/0214256 A1 | 9/2005 | Megede et al. |
| 2006/0088909 A1 | 4/2006 | Compans et al. |
| 2006/0099225 A1 | 5/2006 | Bavari et al. |
| 2006/0127413 A1 | 6/2006 | Sutter et al. |
| 2006/0216702 A1 | 9/2006 | Compans et al. |

(Continued)

FOREIGN PATENT DOCUMENTS

| EP | 0538496 A1 | 5/1993 |
| EP | 2402451 A2 | 1/2012 |

(Continued)

OTHER PUBLICATIONS

Coler et al. 2009 (Adjuvants for Malaria vaccines; Parasite Immunology 31:520-528). (Year: 2009).*

U.S. Pat. No. 11,052,148, B2, U.S. Appl. No. 16/305,305, Guirakhoo et al., Jul. 6, 2021.

U.S. Pat. No. 11,278,607, B2, U.S. Appl. No. 16/068,527, Robinson et al., Mar. 22, 2022.

U.S. Pat. No. 11,311,612, B2, U.S. Appl. No. 16/648,693, Guirakhoo et al., filed Apr. 6, 2022.

(Continued)

*Primary Examiner* — Mary Maille Lyons
(74) *Attorney, Agent, or Firm* — Knowles Intellectual Property Strategies, LLC

(57) ABSTRACT

The compositions and methods are described for generating an immune response to a *Plasmodium* antigen. The compositions and methods described herein relate to a modified vaccinia Ankara (MVA) vector encoding one or more viral antigens for generating a protective immune response to malaria by expressing the *Plasmodium* antigen in the subject to which the MVA vector is administered. The compositions and methods of the present invention are useful both prophylactically and therapeutically and may be used to prevent and/or treat malaria.

17 Claims, 3 Drawing Sheets

Specification includes a Sequence Listing.

(56) References Cited

U.S. PATENT DOCUMENTS

| | | |
|---|---|---|
| 2007/0160627 A1 | 7/2007 | Staib et al. |
| 2008/0193483 A1 | 8/2008 | Moss et al. |
| 2008/0199493 A1 | 8/2008 | Picker et al. |
| 2009/0092628 A1 | 4/2009 | Mullins et al. |
| 2010/0047277 A1 | 2/2010 | Compans et al. |
| 2010/0143402 A1 | 6/2010 | Moss et al. |
| 2010/0196419 A1 | 8/2010 | Compans et al. |
| 2010/0330190 A1 | 12/2010 | Compans et al. |
| 2011/0104199 A1 | 5/2011 | Moss et al. |
| 2012/0052082 A1 | 3/2012 | Compans et al. |
| 2012/0219576 A1 | 8/2012 | Branco et al. |
| 2013/0101618 A1 | 4/2013 | Sullivan et al. |
| 2013/0280215 A1 | 10/2013 | Robinson |
| 2014/0322265 A1 | 10/2014 | Chaplin et al. |
| 2015/0299290 A1 | 10/2015 | Boons et al. |
| 2016/0040135 A1 | 2/2016 | Moss et al. |
| 2016/0144011 A1 | 5/2016 | Collins et al. |
| 2016/0251406 A1 | 9/2016 | Schlom et al. |
| 2017/0304427 A1 | 10/2017 | Volkmann et al. |
| 2019/0030157 A1 | 1/2019 | Guirakhoo et al. |
| 2019/0117758 A1 | 4/2019 | Robinson et al. |
| 2019/0184009 A1 | 6/2019 | Guirakhoo et al. |
| 2019/0290745 A1 | 9/2019 | Robinson et al. |
| 2019/0382453 A1 | 12/2019 | Robinson |
| 2023/0040403 A1 | 2/2023 | Robinson et al. |
| 2024/0156940 A1 | 5/2024 | Robinson et al. |

FOREIGN PATENT DOCUMENTS

| | | | |
|---|---|---|---|
| WO | WO 1994/012617 A1 | 6/1994 | |
| WO | WO 1998/008539 A1 | 3/1998 | |
| WO | WO 1999/063062 A1 | 12/1999 | |
| WO | WO 2000/003030 A1 | 1/2000 | |
| WO | WO 2002/072754 A2 | 9/2002 | |
| WO | WO 2003/078640 A2 | 9/2003 | |
| WO | WO 2003/097845 A1 | 11/2003 | |
| WO | WO 2004/048582 A2 | 6/2004 | |
| WO | WO 2005/048957 A2 | 6/2005 | |
| WO | WO 2006/026667 A2 | 3/2006 | |
| WO | WO 2007/012691 A1 | 2/2007 | |
| WO | WO 2008/142479 A2 | 11/2008 | |
| WO | WO 2010/062757 A1 | 6/2010 | |
| WO | WO 2011/047031 A2 | 4/2011 | |
| WO | WO 2011/103417 A2 | 8/2011 | |
| WO | WO 2013/059498 A1 | 5/2013 | |
| WO | WO 2014/005958 A1 | 1/2014 | |
| WO | WO 2015/009946 A1 | 1/2015 | |
| WO | WO 2015/066715 A1 | 5/2015 | |
| WO | WO 2015/175340 A1 | 11/2015 | |
| WO | WO 2016/034678 A2 | 3/2016 | |
| WO | WO 2016/068919 A1 | 5/2016 | |
| WO | WO 2016/115116 A1 | 7/2016 | |
| WO | WO 2017/120577 A1 | 7/2017 | |
| WO | WO 2017/136419 A1 | 8/2017 | |
| WO | WO 2017/143016 A1 | 8/2017 | |
| WO | WO 2017/210181 A1 | 12/2017 | |
| WO | WO 2018/195447 A1 | 10/2018 | |
| WO | WO 2019/018501 A1 | 1/2019 | |
| WO | WO 2019/040846 A1 | 2/2019 | |
| WO | WO 2019/060356 A1 | 3/2019 | |
| WO | WO 2020/247547 A1 | 12/2020 | |

OTHER PUBLICATIONS

U.S. Pat. No. 11,701,418, B2, U.S. Appl. No. 15/543,139, Robinson et al., filed Jul. 18, 2023.

U.S. Pat. No. 11,413,341, B2, U.S. Appl. No. 16/796,350, Robinson et al., filed Aug. 16, 2022.

U.S. Pat. No. 11,638,750, B2, U.S. Appl. No. 17/000,768, Guirakhoo et al., filed May 5, 2023.

U.S. Pat. No. 11,801,299, B2, U.S. Appl. No. 17/368,761, Guirakhoo et al., filed Oct. 31, 2023.

U.S. Pat. No. 11,857,611, B2, U.S. Appl. No. 17/726,254, Guirakhoo et al., filed Jan. 2, 2024.

U.S. Pat. No. 11,896,657, B2, U.S. Appl. No. 17/584,231, Robinson et al., filed Feb. 13, 2024.

U.S. Pat. No. 11,897,919, B2, U.S. Appl. No. 17/409,574, Robinson et al., filed Feb. 13, 2024.

Adu-Gyamfi et al., "The Ebola Virus Matrix Protein Penetrates into the Plasma Membrane," J. Infect. Dis., vol. 210, No. 1, pp. 99-110, Jan. 7, 2014.

Alharbi et al., "Enhancing cellular immunogenicity of MVA-vectored vaccines by utilizing the F11 lendogenous promoter", Vaccine, 34(1), 49-55, 2015.

Antoine et al., "The complete genomic sequence of the modified vaccinia ankara strain: Comparison with other orthpoxviruses", Virology, 244, 365-396, 1998.

Brault, A.C., Domi, A., McDonald, E. et al., "A Zika Vaccine Targeting NS1 Protein Protects Immunocompetent Adult Mice in a Lethal Challenge Model," Sci Rep 7, 14769, https://doi.org/10.1038/s41598-017-15039-8, 2017.

Cavenaugh, J.S. et al., Partially Randomized, Non-Blinded Trial of DNA and MVA Therapeutic 4, 17,22,23 Vaccines Based on Hepatitis B Vims Surface Protein for Chronic HBV Infection. Plos ONE., vol. 6, Issue 2, Feb. 15, 2011.

Coler et al., "Adjuvants for Malaria vaccines," Parasite Immunology, 31:520-528, 2009.

Domi, A., Feldmann, F., Basu, R. et al., "A Single Dose of Modified Vaccinia Ankara expressing Ebola Virus Like Particles Protects Nonhuman Primates from Lethal Ebola Virus Challenge," Sci Rep 8, 864, https://doi.org/10.1038/s41598-017-19041-y, 2018.

Earl et al., "Recombinant modified vaccinia virus ankara provides durable protection against disease caused by immunodeficiency virus as well as long term immunity to an orthopoxvirus in a non-human primate," Virology, 366(1), 84-87, 2007.

GenBank Accession AFV31202, Glycoprotein [Marburg marburgvirus], 2013.

Goepfert PA et al., National Institutes of Allergy and Infectious Diseases HIV Vaccines Trials Network., "Specificity and 6-month durability of immune responses induced by DNA and recombinant modified vaccinia Ankara vaccines expressing HIV-1 virus-like particles", J Infect Dis., 210(1):99-110. doi: 10.1093/infdis/jiu003. Epub Jan. 7, 2014. PMID: 24403557; PMCID: PMC4072895, Jul. 1, 2014.

Goepfert PA, et al., "National Institute of Allergy and Infectious Diseases HIV Vaccine Trials Network. Phase 1 safety and immunogenicity testing of DNA and recombinant modified vaccinia Ankara vaccines expressing HIV-1 virus-like particles", J Infect Dis., 203(5):610-9. doi: 10.1093/infdis/jiq105. Epub Jan. 31, 2011. PMID: 21282192; PMCID: PMC3072720, Mar. 1, 2011.

International Search Report and Written Opinion for PCT/US2018/051652, dated Feb. 11, 2019.

Iyer, S.S et al., "Codelivery of Envelope Protein in Alum with MVA Vaccine Induces CXCR3-Biased CXCR5 + and CXCR5 − CD4 T Cell Responses in Rhesus Macaques", The Journal of Immunology, US, vol. 195, No. 3, doi: 10.4049/jimmunol.1500083, ISSN 0022-1767, pp. 994-1005, Jun. 26, 2015.

Mackett et al., "Vaccinia virus expression vectors", J. Gen. Virology, 67, 2067-2082, 1986.

Malherbe, Delphine C. et al., "Modified vaccinia Ankara vaccine expressing Marburg virus-like particles protects guinea pigs from lethal Marburg virus infection", Vaccines, 5(1), 78, 2020.

Manuel, E.R. et al., "Intergenic region 3 of modified vaccinia ankara is a functional site for insert gene expression and allows for potent antigenA-specific immune responses", Virology, Elsevier, Amsterdam, NL, 2010, 403(2), pp. 155-162, Aug. 1, 2010.

Mittler et al., "The Cytoplasmic Domain of Marburg Virus GP Modulates Early Steps of Viral Infection," Journal of Virology, vol. 85, No. 6, pp. 8188-8196, Jun. 15, 2011.

Moss et al., "Reflections on the early development of poxvirus vectors", Vaccine, 31(39), 4220-4222, 2013.

Orubu et al., "Expression and cellular immunogenicity of a transgenic antigen driven by endogenous poxviral early promoters at their authentic loci in MVA", PLOS One, 7(6), e40167 doi: 10.1371/journal.pone.0040167, 2012.

(56) References Cited

OTHER PUBLICATIONS

Salvato et al., "A Single Dose of Modified Vaccinia Ankara Expressing Lassa Virus-like Particles Protects Mice from Lethal Intracerebral Virus Challenge", Pathogens, 8:133, 2019.

Staib et al., "Transient host range selection for genetic engineering of modified vaccinia virus ankara", Biotechniques, 28, 1137-1148, 2000.

Swenson et al., "Generation of Marburg virus-like particles by co-expression of glycoprotein and matrix protein", FEMS Immunology and Medical Microbiology, 40(1), pp. 27-31, 2004.

Thompson, M. et al., "DNA/MVA Vaccination of HIV-1 Infected Participants with Viral Suppression on Antiretroviral Therapy, followed by Treatment Interruption: Elicitation of Immune Responses without Control of Re-Emergent Virus", PLoS ONE, 11(10): e0163164, https://doi.org/10.1371/journal.pone.0163164, 2016.

Timm et al., "Genetic stability of recombinant MVA-BN", Vaccine, 24, 4618-4621, 2006.

Urata, S. and Yasuda, J., "Cis- and cell-type-dependent trans-requirements for Lassa virus-like particle production", J. Gen. Virol., 96 Pt 7, 1626-1635, 2015.

Vietheer et al., "Immunizations with chimeric hepatitis B virus-like particles to induce potential anti-hepatitis C virus neutralizing antibodies", Antiviral Therapy, 12, 477-487, 2007.

Wang et al., "Modified H5 promoter improves stability of insert genes while maintaining immunogenicity during extended passage of genetically engineered MVA vaccines", Vaccine, 28(6): 1547, Feb. 10, 2010.

Wyatt et al., "Development of a replication-deficient recombinant vaccinia virus vaccine effective against parainfluenza virus 3 infection in an animal model", Vaccine, 14(15), 1451-1458, 1996.

Xiaoying, Shen et al., "HIV gp120 and Modified Vaccinia Virus Ankara (MVA) gp140 Boost Immunogens Increase Immunogenicity of a DNA/MVA HIV-1 Vaccine", Journal of Virology., US, vol. 91, No. 24, doi: 10.1128/JVI.01077-17, ISSN 0022-538X, Dec. 15, 2017.

Ye, L. et al., "Ebola virus like particles produced in insect cells exhibit dendritic cell stimulating activity and induce neutralizing antibodies", Virol., 351, 260-270, 2006.

* cited by examiner

COMPOSITIONS AND METHODS FOR GENERATING AN IMMUNE RESPONSE TO TREAT OR PREVENT MALARIA

CROSS REFERENCE TO RELATED APPLICATIONS

This application is a continuation of U.S. patent application Ser. No. 17/726,254, filed Apr. 21, 2022, which is a continuation of U.S. patent application Ser. No. 16/648,693, filed Mar. 19, 2020, which is a national stage application under 35 U.S.C § 371 of International Application No. PCT/US2018/051652, filed Sep. 19, 2018, which claims the benefit of U.S. Provisional Application No. 62/560,405, filed Sep. 19, 2017. The entirety of each of these applications is hereby incorporated by reference for all purposes.

FIELD OF THE INVENTION

The compositions and methods described herein relate to compositions, including vaccine compositions, for generating an immune response to malaria; methods of manufacture; and methods of use thereof. The compositions and methods of the present invention are useful both prophylactically and therapeutically.

INCORPORATION BY REFERENCE

The contents of the xml file named "19101-019US3_ST26_2023-12-20" which was created on Dec. 20, 2023, and is 32.7 KB in size, are hereby incorporated by reference in their entirety.

BACKGROUND OF THE INVENTION

Malaria is one of the most prevalent infections in tropical and subtropical area throughout the world. Malaria infections lead to severe illnesses in hundreds of millions of individuals worldwide, leading to death in millions of individuals, primarily in developing and emerging countries every year. It is a mosquito-borne blood disease caused by a *Plasmodium* parasite transmitted to humans through the bite of the *Anopheles* mosquito. The widespread occurrence and elevated incidence of malaria are a consequence of the increasing numbers of drug-resistant parasites and insecticide-resistant parasite vectors. Other factors include environmental and climatic changes, civil disturbances, and increased mobility of populations.

Malaria is caused by the mosquito-borne hematoprotozoan parasites belonging to the genus *Plasmodium*. Four species of *Plasmodium* protozoa (*P. falciparum, P. vivax, P. ovale* and *P. malariae*) are responsible for the disease in man; many others cause disease in animals, such as *P. yoelii* and *P. berghei* in mice. *P. falciparum* accounts for the majority of human infections and is the most lethal type, sometimes called "tropical malaria". Malaria parasites have a life cycle consisting of several stages. Each stage is able to induce specific immune responses directed against the corresponding occurring stage-specific antigens. A current area of focus is development of vaccines that elicit immunity against the sporozoite stage pathogen. The sporozoite grows in the saliva of infected mosquitoes and is transferred to the human during the mosquito bite. The sporozoite travels thorough the blood stream to the liver where it enters hepatocytes and multiplies. Sporozoites are covered with many copies of the circumsporozoite coat protein (CS). Antibodies that bind to CS proteins can neutralize the organism and prevent liver invasion, so agents that elicit potent and long-lasting anti-CS responses are expected to be useful malaria vaccines.

There is no US approved vaccine for humans to prevent or treat malaria. Currently there are two vaccines in clinical trials that seek to prevent malaria infections via the CS neutralization mechanism. Most malaria vaccines are based on subunit proteins which have solubility problems in expression systems such as bacteria and yeast. Subunit proteins are also poorly immunogenic. What is needed are immunogenic vaccine compositions and methods of use to provide the most effective immune responses possible and prevent or treat malaria.

SUMMARY OF THE INVENTION

The compositions and methods of the invention described herein are useful for generating an immune response to prevent or treat malaria in a subject in need thereof. Advantageously, the compositions and methods may be used prophylactically to immunize a subject against *Plasmodium* antigens or used therapeutically to treat or ameliorate the onset and severity of disease in a subject in need thereof.

Expression of subunit proteins by MVA vectors that assemble into virus-like particles (VLP) provide immunogenic compositions for administration to generate a protective immune response to malaria. MVA-VLP compositions express antigens associated with three stages of *Plasmodium* lifecycle for the purpose of 1) halting the parasite at initial infection, 2) during high parasite burden in the RBC cycle phase and 3) in the mosquito transmission phase.

In a first aspect, the present invention is a composition comprising a) a recombinant modified vaccinia Ankara (MVA) vector comprising a *Plasmodium* antigen-encoding sequence under the control of a promoter compatible with poxvirus expression systems.

In one embodiment, the recombinant modified vaccinia Ankara (MVA) vector comprises a *Plasmodium* antigen-encoding sequence and a matrix protein-encoding sequence (matrix protein sequence), wherein both the *Plasmodium* antigen sequence and matrix protein sequence are under the control of promoters compatible with poxvirus expression systems.

In one embodiment, the *Plasmodium* antigen sequence is selected from *Plasmodium* blood or liver stage antigen or a combination thereof.

In one embodiment, the *Plasmodium* antigen is a sporozite stage antigen selected from CSP, TRAP or STARP or a combination thereof.

In one embodiment, the *Plasmodium* antigen is a merozoite stage antigen selected from MSP-1, MSP-2, MSP-3, GLURP, EBA-140, EBA-175, RAP1, RAP2, or AMA-1 or a combination thereof.

In one embodiment, the *Plasmodium* antigen is a gametocyte stage antigen selected from Pfs25, Pfs230, PfsSEA-1, Pfs45/48, Pfs SEA-1 or a combination thereof.

In one embodiment, the *Plasmodium* antigen is selected from CPBAg1, AgAPN1, SGS or a combination thereof.

In one embodiment, the *Plasmodium* antigen is a liver stage antigen selected from LSA1, LSA3, SALSA or a combination thereof.

In one embodiment, the *Plasmodium* antigen sequence and the matrix protein sequence are inserted into one or more deletion sites of the MVA vector.

In one embodiment, the matrix protein is selected from Marburg virus VP40 matrix protein, Ebola virus VP40 matrix protein, human immunodeficiency virus type 1 (HIV-1) matrix protein (Clade A, B or C) or Lassa virus matrix Z protein.

In one embodiment, the Ebola virus VP40 matrix protein is selected from Zaire Ebola virus VP40 or Sudan Ebola virus VP40.

In one embodiment, the *Plasmodium* antigen sequence and the matrix protein sequence are inserted into the MVA vector in a natural deletion site, a modified natural deletion site, or between essential or non-essential MVA genes.

In another embodiment, the *Plasmodium* antigen sequence and the matrix protein sequence are inserted into the same natural deletion site, a modified natural deletion site, or between the same essential or non-essential MVA genes.

In another embodiment, the *Plasmodium* antigen sequence is inserted into a deletion site selected from I, II, III, IV, V, or VI and the matrix protein sequence is inserted into a deletion site selected from I, II, III, IV, V, or VI.

In another embodiment, the *Plasmodium* antigen sequence and the matrix protein sequence are inserted into different natural deletion sites, different modified deletion sites, or between different essential or non-essential MVA genes.

In another embodiment, the *Plasmodium* antigen is inserted in a first deletion site and matrix protein sequence is inserted into a second deletion site.

In a particular embodiment, the *Plasmodium* antigen is inserted between two essential and highly conserved MVA genes; and the matrix protein sequence is inserted into a restructured and modified deletion III.

In a particular embodiment, the *Plasmodium* antigen sequence is inserted between two essential and highly conserved MVA genes to limit the formation of viable deletion mutants.

In a particular embodiment, the *Plasmodium* antigen protein sequence is inserted between MVA genes, 18R and G1L.

In a particular embodiment, the *Plasmodium* antigen protein sequence is inserted between MVA genes, A50R and B1R.

In a particular embodiment, the matrix protein sequence is inserted between MVA genes, 18R and G1L.

In a particular embodiment, the matrix protein sequence is inserted between MVA genes, A50R and B1R.

In one embodiment, the *Plasmodium* antigen protein sequence is expressed with a matrix protein sequence as a fusion protein.

In a particular embodiment, the *Plasmodium* antigen/matrix protein fusion protein sequence is inserted between MVA genes, 18R and G1L.

In a particular embodiment, the *Plasmodium* antigen/matrix protein fusion protein sequence is inserted between MVA genes, A50R and B1R.

In one embodiment, the promoter is selected from the group consisting of Pm2H5, Psyn II, and mH5 promoters or combinations thereof.

In one embodiment, the recombinant MVA viral vector expresses a *Plasmodium* antigen and matrix proteins that assemble into VLPs.

In a second aspect, the present invention provides a pharmaceutical composition comprising the recombinant MVA vector of the present invention and/or *Plasmodium* antigen and a pharmaceutically acceptable carrier.

In one embodiment, the recombinant MVA vector is formulated for intraperitoneal, intramuscular, intradermal, epidermal, mucosal, or intravenous administration.

In a third aspect, the present invention provides a method of inducing a protective immune response to malaria in a subject in need thereof, said method comprising:

a) administering a composition comprising an immunogenic vector expressing *Plasmodium* antigen to the subject in an amount sufficient to induce an immune response or boost a previously induced immune response.

In one embodiment, the immune response is a humoral immune response, a cellular immune response or a combination thereof.

In a particular embodiment, the immune response comprises production of binding antibodies against the *Plasmodium* antigen.

In a particular embodiment, the immune response comprises production of neutralizing antibodies against the *Plasmodium* antigen.

In a particular embodiment, the immune response comprises production of non-neutralizing antibodies against the *Plasmodium* antigen.

In a particular embodiment, the immune response comprises production of a cell-mediated immune response against the *Plasmodium* antigen.

In a particular embodiment, the immune response comprises production of neutralizing and non-neutralizing antibodies against the *Plasmodium* antigen.

In a particular embodiment, the immune response comprises production of neutralizing antibodies and cell-mediated immunity against the *Plasmodium* antigen.

In a particular embodiment, the immune response comprises production of non-neutralizing antibodies and cell-mediated immunity against the *Plasmodium* antigen.

In a particular embodiment, the immune response comprises production of neutralizing antibodies, non-neutralizing antibodies, and cell-mediated immunity against the *Plasmodium* antigen.

In a fourth aspect, the present invention provides a method of treating malaria or reducing symptoms of malaria comprising administering the recombinant MVA vector of the present invention to a subject in need thereof in an effective amount to treat malaria.

In a fifth aspect, the present invention provides a method of preventing malaria in a subject, said method comprising administering the recombinant MVA vector of the present invention to the subject in a prophylactically effective amount.

DETAILED DESCRIPTION OF THE INVENTION

Figure 1:
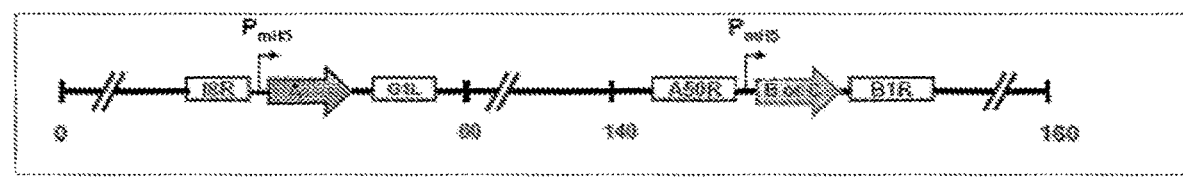
FIG. 1 is a simple line drawing illustrating the design of the *Plasmodium* antigen expressing MVA vectors. Positions are given in kilobase pairs and diagram is not to scale. Insert A between 18R and G1L in various embodiments contains a *Plasmodium* antigen encoding sequence selected from CSP, MSP-1, MSP-2, MSP-3, GLURP, EBA-175, Pfs25, Pfs230, PfsSEA-1, Pfs45/48, Pfs SEA-1, CPBAg1, AgAPN1, SGS. Insert B between A50R and B1R in various embodiments contains a matrix protein selected from Vp40 protein of the Zaire Ebola virus, Vp40 protein of the Sudan Ebola virus, Vp40 protein of the Marburg virus, Z protein of Lassa virus or Gag protein of HIV (clade A, B or C). Insert B between A50R and B1R in various embodiments contains a fusion protein-encoding sequence encoding a *Plasmodium* antigen and a matrix protein listed here.
Figure 2A:
FIGS. 2A-2E provide graphs showing antibody response to CSP as shown by ELISA. Graphs show binding of CSP-IgG at 1/100 to 1/64000 dilutions for sera from mice vaccinated with MVA-CSPNR (FIG. 2A and FIG. 2B), MVA-CSP21R (FIG. 2C), MVA-Gag.CSPNR (FIG. 2D) and control mice vaccinated with recombinant CSP+ alum adjuvant (FIG. 2E).
Figure 2B:
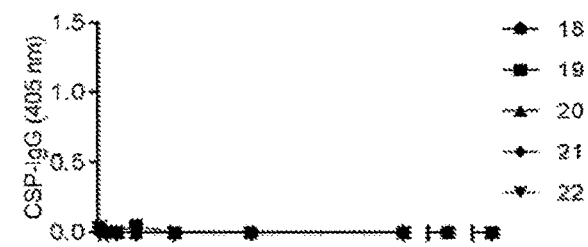
Figure 2C:
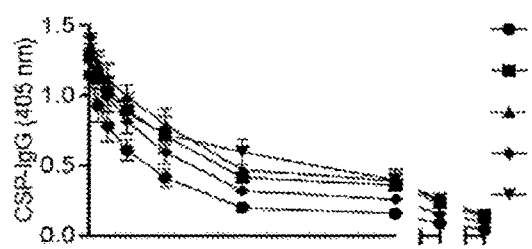
Figure 2D:
Figure 2E:
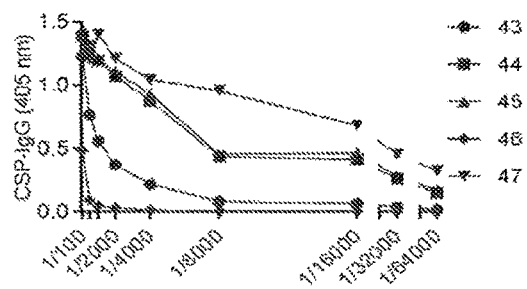
Figure 3A:
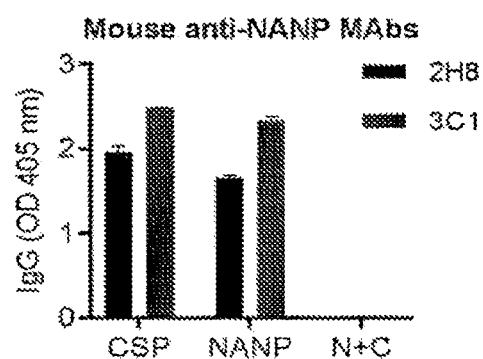
FIGS. 3A and 3B provides graphs showing the binding activity of Mouse anti-NANP monoclonal antibodies (clones 2H8 and 3C1) to full-length CSP and a NANP (asparagine (N)-alanine (A)-asparagine (N)-proline (P)) repeat polymer (FIG. 3A). Antibodies raised in rabbits to recombinant truncated CSP do not react with NANP repeats (FIG. 3B).
Figure 3B:
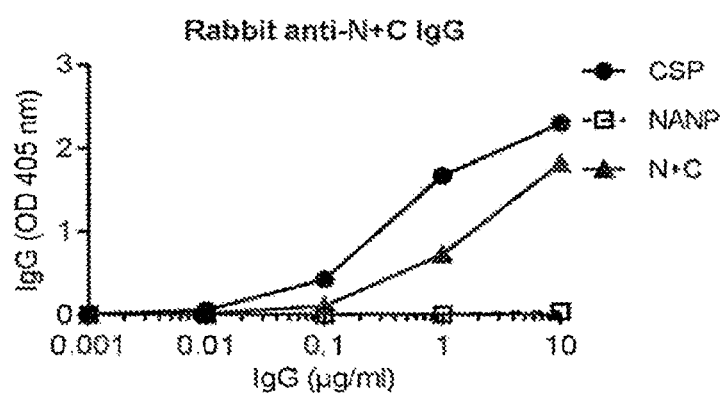
Figure 4A:
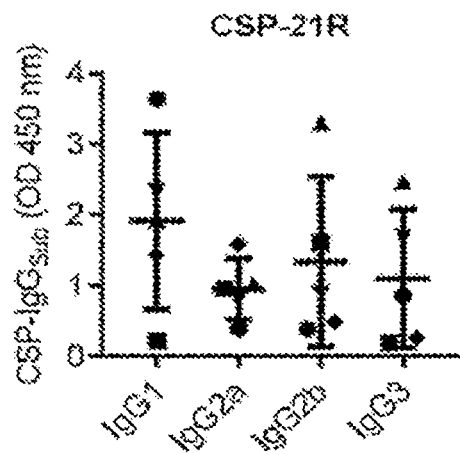
FIGS. 4A-4E provides graphs showing further testing for IgG subclass reactivity, specifically to CSP-21R (FIG. 4A) and recombinant CSP (FIG. 4B) at 1/1000 dilution. Sera were also tested for the ability to fix human complement (FIG. 4C) and the ability to react with human Fc receptors FcγRIIa (FIG. 4D) and FcγRIIIa (FIG. 4E).
Figure 4B:
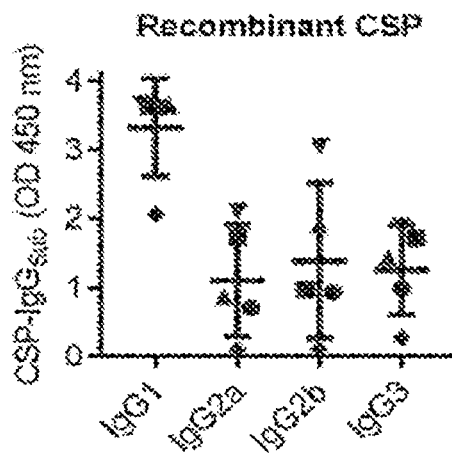
Figure 4C:
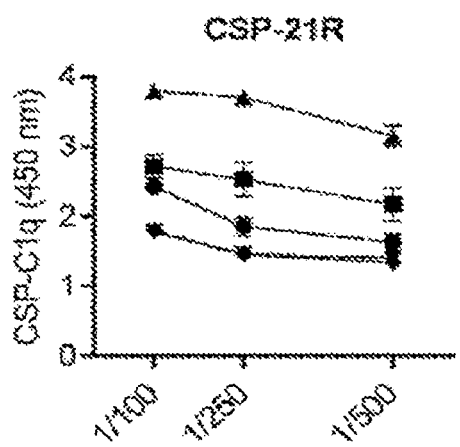
Figure 4D:
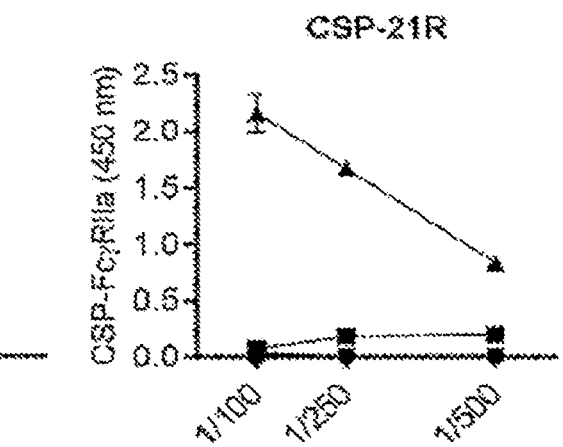
Figure 4E:
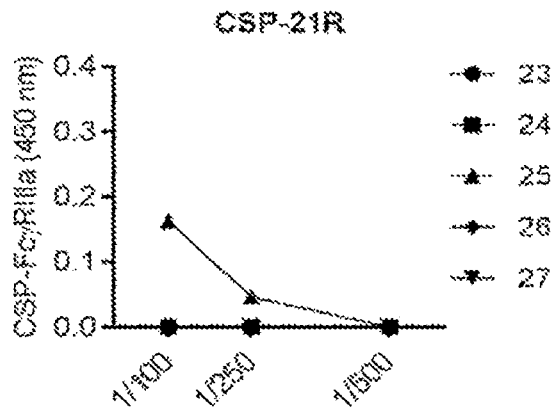

Compositions and methods are provided to produce an immune response to a *Plasmodium* antigen, in a subject in need thereof. The compositions and methods of the present invention can be used to prevent or delay symptoms of malaria infection or to treat malaria in a subject in need thereof.

Ideal immunogenic compositions or vaccines have the characteristics of safety, efficacy, scope of protection and longevity, however, compositions having fewer than all of these characteristics may still be useful in preventing malaria or limiting symptoms or disease progression in an exposed subject treated prior to the development of symptoms. In one embodiment the present invention provides a vaccine that permits at least partial, if not complete, protection after a single immunization.

In one embodiment, the composition is a recombinant vaccine or immunogenic vector that comprises one or more nucleic acid sequences *Plasmodium* antigens or immunogenic fragments thereof.

In one embodiment, the vector expresses proteins that form VLPs and generate an immune response to a *Plasmodium* antigen or immunogenic fragment thereof.

In exemplary embodiments, the immune responses are long-lasting and durable so that repeated boosters are not required, but in one embodiment, one or more administrations of the compositions provided herein are provided to boost the initial primed immune response.

I. Definitions

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a peptide" includes a plurality of peptides. Thus, for example, a reference to "a method" includes one or more methods, and/or steps of the type described herein and/or which will become apparent to those persons skilled in the art upon reading this disclosure.

The term "antigen" refers to a substance or molecule, such as a protein, or fragment thereof, that is capable of inducing an immune response.

The term "binding antibody" or "bAb" refers to an antibody which either is purified from, or is present in, a body fluid (e.g., serum or a mucosal secretion) and which recognizes a specific antigen. As used herein, the antibody can be a single antibody or a plurality of antibodies. Binding antibodies comprise neutralizing and non-neutralizing antibodies.

The term "cell-mediated immune response" refers to the immunological defense provided by lymphocytes, such as the defense provided by sensitized T cell lymphocytes when they directly lyse cells expressing foreign antigens and secrete cytokines (e.g., IFN-gamma), which can modulate macrophage and natural killer (NK) cell effector functions and augment T cell expansion and differentiation. The cellular immune response is the 2nd branch of the adaptive immune response.

The term "conservative amino acid substitution" refers to substitution of a native amino acid residue with a non-native residue such that there is little or no effect on the size, polarity, charge, hydrophobicity, or hydrophilicity of the amino acid residue at that position, and without resulting in substantially altered immunogenicity. For example, these may be substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a parental polypeptide.

The term "deletion" in the context of a polypeptide or protein refers to removal of codons for one or more amino acid residues from the polypeptide or protein sequence, wherein the regions on either side are joined together. The term deletion in the context of a nucleic acid refers to removal of one or more bases from a nucleic acid sequence, wherein the regions on either side are joined together.

The term "Ebola virus" refers to a virus of species Zaire ebolavirus and has the meaning given to it by the International Committee on Taxonomy of Viruses as documented in (Kuhn, J. H. et al. 2010 Arch Virol 155:2083-2103).

The term "fragment" in the context of a proteinaceous agent refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a peptide, polypeptide or protein. In one embodiment the fragment constitutes at least 10%, 20%, 30%, 40%, 50%, 60%, 70%, 80%, or 90% of the entire length of the reference polypeptide. In one embodiment, a fragment of a full-length protein retains activity of the full-length protein. In another embodiment, the fragment of the full-length protein does not retain the activity of the full-length protein.

The term "fragment" in the context of a nucleic acid refers to a nucleic acid comprising an nucleic acid sequence of at least 2 contiguous nucleotides, at least 5 contiguous nucleotides, at least 10 contiguous nucleotides, at least 15 contiguous nucleotides, at least 20 contiguous nucleotides, at least 25 contiguous nucleotides, at least 30 contiguous nucleotides, at least 35 contiguous nucleotides, at least 40 contiguous nucleotides, at least 50 contiguous nucleotides, at least 60 contiguous nucleotides, at least 70 contiguous nucleotides, at least contiguous 80 nucleotides, at least 90 contiguous nucleotides, at least 100 contiguous nucleotides, at least 125 contiguous nucleotides, at least 150 contiguous nucleotides, at least 175 contiguous nucleotides, at least 200 contiguous nucleotides, at least 250 contiguous nucleotides, at least 300 contiguous nucleotides, at least 350 contiguous nucleotides, or at least 380 contiguous nucleotides of the nucleic acid sequence encoding a peptide, polypeptide or protein. In one embodiment the fragment constitutes at least 10%, 20%, 30%, 40%, 50%, 60%, 70%, 80%, or 90% of the entire length of the reference nucleic acid sequence. In a preferred embodiment, a fragment of a nucleic acid encodes a peptide or polypeptide that retains activity of the full-length protein. In another embodiment, the fragment encodes a peptide or polypeptide that of the full-length protein does not retain the activity of the full-length protein.

As used herein, the phrase "heterologous sequence" refers to any nucleic acid, protein, polypeptide, or peptide sequence which is not normally associated in nature with another nucleic acid or protein, polypeptide, or peptide sequence of interest.

As used herein, the phrase "heterologous gene insert" refers to any nucleic acid sequence that has been or is to be inserted into the recombinant vectors described herein. The heterologous gene insert may refer to only the gene product encoding sequence or may refer to a sequence comprising a promoter, a gene product encoding sequence (such as GP, VP, or Z), and any regulatory sequences associated or operably linked therewith.

The term "homopolymer stretch" refers to a sequence comprising at least four of the same nucleotides uninterrupted by any other nucleotide, e.g., GGGG or TTTTTTT.

The term "humoral immune response" refers to the stimulation of Ab production. Humoral immune response also refers to the accessory proteins and events that accompany antibody production, including T helper cell activation and cytokine production, affinity maturation, and memory cell generation. The humoral immune response is one of two branches of the adaptive immune response.

The term "humoral immunity" refers to the immunological defense provided by antibody, such as neutralizing Ab that can directly bind a *Plasmodium* antigen; or, binding Ab that identifies a neoplastic cell for killing by such innate immune responses as complement (C')-mediated lysis, phagocytosis, and natural killer cells.

The term "immunogenic composition" is a composition that comprises an antigenic molecule where administration of the composition to a subject results in the development in the subject of a humoral and/or a cellular immune response to the antigenic molecule of interest.

The term "immune response" refers to any response to an antigen or antigenic determinant by the immune system of a subject (e.g., a human). Exemplary immune responses include humoral immune responses (e.g., production of antigen-specific antibodies) and cell-mediated immune responses (e.g., production of antigen-specific T cells). Assays for assessing an immune response are known in the art and may comprise in vivo assays, such as assays to measure antibody responses and delayed type hypersensitivity responses. In an embodiment, the assay to measure antibody responses primarily may measure B-cell function as well as B-cell/T-cell interactions. For the antibody response assay, antibody titers in the blood may be compared following an antigenic challenge. As used herein, "antibody titers" can be defined as the highest dilution in post-immune sera that resulted in a value greater than that of pre-immune samples for each subject. The in vitro assays may comprise determining the ability of cells to divide, or to provide help for other cells to divide, or to release lymphokines and other factors, express markers of activation, and lyse target cells. Lymphocytes in mice and man can be compared in in vitro assays. In an embodiment, the lymphocytes from similar sources such as peripheral blood cells, splenocytes, or lymph node cells, are compared. It is possible, however, to compare lymphocytes from different sources as in the non-limiting example of peripheral blood cells in humans and splenocytes in mice. For the in vitro assay, cells may be purified (e.g., B-cells, T-cells, and macrophages) or left in their natural state (e.g., splenocytes or lymph node cells). Purification may be by any method that gives the desired results. The cells can be tested in vitro for their ability to proliferate using mitogens or specific antigens. The ability of cells to divide in the presence of specific antigens can be determined using a mixed lymphocyte reaction (MLR) assay. Supernatant from the cultured cells can be tested to quantitate the ability of the cells to secrete specific lymphokines. The cells can be removed from culture and tested for their ability to express activation antigens. This can be done by any method that is suitable as in the non-limiting example of using antibodies or ligands which bind to the activation antigen as well as probes that bind the RNA coding for the activation antigen.

The term "improved therapeutic outcome" relative to a subject diagnosed as having malaria refers to a slowing or diminution in the symptoms, or detectable symptoms associated with malaria.

The term "inducing an immune response" means eliciting a humoral response (e.g., the production of antibodies) or a cellular response (e.g., the activation of T cells) directed against a *Plasmodium* antigen in a subject to which the composition (e.g., a vaccine) has been administered.

The term "insertion" in the context of a polypeptide or protein refers to the addition of one or more non-native amino acid residues in the polypeptide or protein sequence. Typically, no more than about from 1 to 6 residues (e.g., 1 to 4 residues) are inserted at any one site within the polypeptide or protein molecule.

The term "Marburg virus" refers to a virus of species Marburg marburgvirus and has the meaning given to it by the International Committee on Taxonomy of Viruses as documented in (Kuhn, J. H. et al. 2010 Arch Virol 155: 2083-2103).

The term "marker" refers to is meant any protein or polynucleotide having an alteration in expression level or activity that is associated with a disease or disorder.

The term "modified vaccinia Ankara," "modified vaccinia ankara," "Modified Vaccinia Ankara," or "MVA" refers to a highly attenuated strain of vaccinia virus developed by Dr. Anton Mayr by serial passage on chick embryo fibroblast cells; or variants or derivatives thereof. MVA is reviewed in (Mayr, A et al. 1975 Infection 3:6-14; Swiss U.S. Pat. No. 568,392).

The term "*Plasmodium* antigen immunogenic fragment" as used herein means an immunogenic poly amino acid containing at least 10 consecutive amino acids of a *Plasmodium* antigen sequence.

The term "neutralizing antibody" or "NAb" refers to an antibody which either is purified from, or is present in, a body fluid (e.g., serum or a mucosal secretion) and which recognizes a specific antigen and inhibits the effect(s) of the antigen in the subject (e.g., a human). As used herein, the antibody can be a single antibody or a plurality of antibodies.

The term "non-neutralizing antibody" or "nnAb" refers to a binding antibody that is not a neutralizing antibody.

"Operably linked." A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "prevent", "preventing" and "prevention" refers to the inhibition of the development of malaria or symptoms thereof.

The term "promoter" refers to a polynucleotide sufficient to direct transcription.

The term "prophylactically effective amount" refers to the amount of a composition (e.g., the recombinant MVA vector or pharmaceutical composition) which is sufficient to result in the prevention of the development, recurrence, or onset of malaria or a symptom thereof.

The term "recombinant" means a polynucleotide of semi-synthetic, or synthetic origin that either does not occur in nature or is linked to another polynucleotide in an arrangement not found in nature.

The term "recombinant," with respect to a viral vector, means a vector (e.g., a viral genome that has been manipulated in vitro, e.g., using recombinant nucleic acid techniques to express heterologous viral nucleic acid sequences.

The term "regulatory sequence" "regulatory sequences" refers collectively to promoter sequences, polyadenylation signals, transcription termination sequences, upstream regulatory domains, origins of replication, internal ribosome entry sites ("IRES"), enhancers, and the like, which collectively provide for the transcription and translation of a coding sequence. Not all of these control sequences need always be present so long as the selected gene is capable of being transcribed and translated.

The term "shuttle vector" refers to a genetic vector (e.g., a DNA plasmid) that is useful for transferring genetic material from one host system into another. A shuttle vector can replicate alone (without the presence of any other vector) in at least one host (e.g., *E. coli*). In the context of MVA vector construction, shuttle vectors are usually DNA plasmids that can be manipulated in *E. coli* and then introduced into cultured cells infected with MVA vectors, resulting in the generation of new recombinant MVA vectors.

The term "silent mutation" means a change in a nucleotide sequence that does not cause a change in the primary structure of the protein encoded by the nucleotide sequence, e.g., a change from AAA (encoding lysine) to AAG (also encoding lysine).

The term "subject" means any mammal, including but not limited to, humans, domestic and farm animals, and zoo, sports, or pet animals, such as dogs, horses, cats, cows, rats, mice, guinea pigs and the like. Determination of those subjects "at risk" can be made by any objective or subjective determination by a diagnostic test or opinion of a subject or health care provider (e.g., genetic test, enzyme or protein marker, marker history, and the like).

The term "Sudan virus" refers to a virus of species Sudan ebolavirus and has the meaning given to it by the International Committee on Taxonomy of Viruses as documented in (Kuhn, J. H. et al. 2010 Arch Virol 155:2083-2103).

The term "surrogate endpoint" means a clinical measurement other than a measurement of clinical benefit that is used as a substitute for a measurement of clinical benefit.

The term "surrogate marker" means a laboratory measurement or physical sign that is used in a clinical or animal trial as a substitute for a clinically meaningful endpoint that is a direct measure of how a subject feels, functions, or survives and is expected to predict the effect of the therapy (Katz, R., NeuroRx 1:189-195 (2004); New drug, antibiotic, and biological drug product regulations; accelerated approval-FDA. Final rule. Fed Regist 57:58942-58960, 1992.).

The term "synonymous codon" refers to the use of a codon with a different nucleic acid sequence to encode the same amino acid, e.g., AAA and AAG (both of which encode lysine). Codon optimization changes the codons for a protein to the synonymous codons that are most frequently used by a vector or a host cell.

The term "therapeutically effective amount" means the amount of the composition (e.g., the recombinant MVA vector or pharmaceutical composition) that, when administered to a mammal for treating malaria, is sufficient to effect such treatment for malaria.

The term "treating" or "treat" refer to the eradication or control of malaria, the reduction or amelioration of the progression, severity, and/or duration of a condition or one or more symptoms caused by malaria resulting from the administration of one or more therapies.

The term "vaccine" means material used to provoke an immune response and confer immunity after administration of the material to a subject. Such immunity may include a cellular or humoral immune response that occurs when the subject is exposed to the immunogen after vaccine administration.

The term "vaccine insert" refers to a nucleic acid sequence encoding a heterologous sequence that is operably linked to a promoter for expression when inserted into a recombinant vector. The heterologous sequence may encode a glycoprotein or matrix protein described here.

The term "virus-like particles" or "VLP" refers to a structure which resembles the native virus antigenically and morphologically.

II. *Plasmodium* Antigens

The compositions of the present invention are useful for inducing an immune response to a *Plasmodium* antigen.

In one embodiment, the *Plasmodium* antigen sequence is selected from *Plasmodium* blood or liver stage antigen or a combination thereof.

In one embodiment, the *Plasmodium* antigen is a sporozite stage antigen selected from CSP, TRAP, or STARP, or a combination thereof.

In one embodiment, the *Plasmodium* antigen is a merozoite stage antigen selected from MSP-1, MSP-2, MSP-3, GLURP, EBA-140, EBA-175, RAP1, RAP2, or AMA-1, or a combination thereof.

In one embodiment, the *Plasmodium* antigen is a gametocyte stage antigen selected from Pfs25, Pfs230, PfsSEA-1, Pfs45/48, Pfs SEA-1, or a combination thereof.

In one embodiment, the *Plasmodium* antigen is selected from CPBAg1, AgAPN1, SGS, or a combination thereof.

In one embodiment, the *Plasmodium* antigen is a liver stage antigen selected from LSA1, LSA3, SALSA, or a combination thereof.

The nucleic acid sequences of many *Plasmodium* antigens are published and are available from a variety of sources, including, e.g., GenBank and PubMed.

In certain embodiments, the one or more genes encodes a polypeptide, or fragment thereof, that is substantially identical (e.g., at least 60%, 65%, 70%, 75%, 80%, 85%, 90%, 95%, 98%, 99%, or even 100% identical) to the selected *Plasmodium* antigen over at least 10, 15, 20, 25, 30, 35, 40, 45, 50, 55, 60, 65, or 70 contiguous residues of the selected *Plasmodium* antigen or immunogenic fragment thereof that retain immunogenic activity.

In certain embodiments, the polypeptide, or the nucleic acid sequence encoding the polypeptide, may have a mutation or deletion (e.g., an internal deletion, truncation of the amino- or carboxy-terminus, or a point mutation).

III. Recombinant Viral Vectors

In one aspect, the present invention is a recombinant viral vector comprising one or more nucleic acid sequences encoding *Plasmodium* antigens or immunogenic fragments thereof. In certain embodiments, the recombinant viral vector is a vaccinia viral vector, and more particularly, an MVA vector, comprising one or more nucleic acid sequences encoding *Plasmodium* antigens or immunogenic fragments thereof.

Vaccinia viruses have also been used to engineer viral vectors for recombinant gene expression and for the potential use as recombinant live vaccines (Mackett, M. et al 1982 PNAS USA 79:7415-7419; Smith, G. L. et al. 1984 Biotech Genet Engin Rev 2:383-407). This entails DNA sequences (genes) which code for foreign antigens being introduced, with the aid of DNA recombination techniques, into the genome of the vaccinia viruses. If the gene is integrated at a site in the viral DNA which is non-essential for the life cycle of the virus, it is possible for the newly produced recombinant vaccinia virus to be infectious, that is to say able to infect foreign cells and thus to express the integrated DNA sequence (EP Patent Applications No. 83,286 and No. 110,385). The recombinant vaccinia viruses prepared in this way can be used, on the one hand, as live vaccines for the prophylaxis of infectious diseases, on the other hand, for the preparation of heterologous proteins in eukaryotic cells.

Several such strains of vaccinia virus have been developed to avoid undesired side effects of smallpox vaccination. Thus, a modified vaccinia Ankara (MVA) has been generated by long-term serial passages of the Ankara strain of vaccinia virus (CVA) on chicken embryo fibroblasts (for review see Mayr, A et al. 1975 Infection 3:6-14; Swiss U.S. Pat. No. 568,392). The MVA virus is publicly available from American Type Culture Collection as ATCC No.: VR-1508. MVA is distinguished by its great attenuation, as demonstrated by diminished virulence and reduced ability to replicate in primate cells, while maintaining good immunogenicity. The MVA virus has been analyzed to determine alterations in the genome relative to the parental CVA strain. Six major deletions of genomic DNA (deletion I, II, III, IV, V, and VI) totaling 31,000 base pairs have been identified (Meyer, H. et al. 1991 J Gen Virol 72:1031-1038). The resulting MVA virus became severely host cell restricted to avian cells.

Furthermore, MVA is characterized by its extreme attenuation. When tested in a variety of animal models, MVA was proven to be avirulent even in immunosuppressed animals. More importantly, the excellent properties of the MVA strain have been demonstrated in extensive clinical trials (Mayr A. et al. 1978 Zentralbl Bakteriol [B] 167:375-390; Stickl et al. 1974 Dtsch Med Wschr 99:2386-2392). During these studies in over 120,000 humans, including high-risk patients, no side effects were associated with the use of MVA vaccine.

MVA replication in human cells was found to be blocked late in infection preventing the assembly to mature infectious virions. Nevertheless, MVA was able to express viral and recombinant genes at high levels even in non-permissive cells and was proposed to serve as an efficient and exceptionally safe gene expression vector (Sutter, G. and Moss, B. 1992 PNAS USA 89:10847-10851). Additionally, novel vaccinia vector vaccines were established on the basis of MVA having foreign DNA sequences inserted at the site of deletion III within the MVA genome (Sutter, G. et al. 1994 Vaccine 12:1032-1040).

Recombinant MVA vaccinia viruses can be prepared as set out in PCT publication WO2017/120577 incorporated by reference herein. A DNA-construct which contains a DNA-sequence which codes for a foreign polypeptide flanked by MVA DNA sequences adjacent to a predetermined insertion site (e.g., between two conserved essential MVA genes such as 18R/GIL; in restructured and modified deletion III; or at other non-essential sites within the MVA genome) is introduced into cells infected with MVA, to allow homologous recombination. Once the DNA-construct has been introduced into the eukaryotic cell and the foreign DNA has recombined with the viral DNA, it is possible to isolate the desired recombinant vaccinia virus in a manner known per se, preferably with the aid of a marker. The DNA-construct to be inserted can be linear or circular. A plasmid or polymerase chain reaction product is preferred. Such methods of making recombinant MVA vectors are described in PCT publication W0/2006/026667 incorporated by reference herein. The DNA-construct contains sequences flanking the left and the right side of a naturally occurring deletion. The foreign DNA sequence is inserted between the sequences flanking the naturally occurring deletion. For the expression of a DNA sequence or gene, it is necessary for regulatory sequences, which are required for the transcription of the gene, to be present on the DNA. Such regulatory sequences (called promoters) are known to those skilled in the art, and include for example those of the vaccinia 11 kDa gene as are described in EP-A-198,328, and those of the 7.5 kDa gene (EP-A-110,385). The DNA-construct can be introduced into the MVA infected cells by transfection, for example by means of calcium phosphate precipitation (Graham et al. 1973 Virol 52:456-467; Wigler et al. 1979 Cell 16:777-785), by means of electroporation (Neumann et al. 1982 EMBO J. 1:841-845), by microinjection (Graessmann et al. 1983 Meth Enzymol 101:482-492), by means of liposomes (Straubinger et al. 1983 Meth Enzymol 101:512-527), by means of spheroplasts (Schaffher 1980 PNAS USA 77:2163-2167) or by other methods known to those skilled in the art.

The MVA vectors described in WO2017/120577 are immunogenic after a single prime or a homologous prime/boost regimen. Other MVA vector designs require a heterologous prime/boost regimen while still other published studies have been unable to induce effective immune responses with MVA vectors. Conversely, these MVA vector are useful in eliciting effective T-cell and antibody immune responses. Furthermore, the utility of an MVA vaccine vector capable of eliciting effective immune responses and antibody production after a single homologous prime boost is significant for considerations such as use, commercialization and transport of materials especially to affected third world locations.

In one embodiment, the present invention is a recombinant viral vector (e.g., an MVA vector) comprising one or more nucleic acid sequences encoding *Plasmodium* antigens or immunogenic fragments thereof. The viral vector (e.g., an MVA vector) may be constructed using conventional techniques known to one of skill in the art. The one or more heterologous gene inserts encode a polypeptide having desired immunogenicity, i.e., a polypeptide that can induce an immune reaction, cellular immunity and/or humoral immunity, in vivo by administration thereof. The gene region of the viral vector (e.g., an MVA vector) where the gene encoding a polypeptide having immunogenicity is introduced is flanked by regions that are indispensable. In the introduction of a gene encoding a polypeptide having immunogenicity, an appropriate promoter may be operatively linked upstream of the gene encoding a polypeptide having desired immunogenicity.

In one aspect, the present invention is a composition comprising a) a recombinant modified vaccinia Ankara (MVA) vector comprising a *Plasmodium* antigen-encoding sequence under the control of a promoter compatible with poxvirus expression systems.

In one embodiment, the *Plasmodium* antigen assembles into virus-like-particles (VLPs) when expressed.

In one embodiment, the present invention is a composition comprising a) a recombinant modified vaccinia Ankara (MVA) vector comprising a *Plasmodium* antigen-encoding sequence and a matrix protein-encoding sequence (matrix protein sequence), wherein both the *Plasmodium* antigen sequence and matrix protein sequence are under the control of promoters compatible with poxvirus expression systems.

In one embodiment, the *Plasmodium* antigen is a sporozite stage antigen selected from CSP, TRAP or STARP, or a combination thereof.

In one embodiment, the *Plasmodium* antigen is a merozoite stage antigen selected from MSP-1, MSP-2, MSP-3, GLURP, EBA-140, EBA-175, RAP1, RAP2, or AMA-1, or a combination thereof.

In one embodiment, the *Plasmodium* antigen is a gametocyte stage antigen selected from Pfs25, Pfs230, PfsSEA-1, Pfs45/48, Pfs SEA-1, or a combination thereof. In one embodiment, the *Plasmodium* antigen is selected from CPBAg1, AgAPN1, SGS, or a combination thereof.

In one embodiment, the *Plasmodium* antigen is a liver stage antigen selected from LSA1, LSA3, SALSA, or a combination thereof.

In one embodiment, the matrix protein is selected from Marburg virus VP40 matrix protein, Ebola virus VP40 matrix protein, human immunodeficiency virus type 1 (HIV-1) matrix protein, or Lassa virus matrix Z protein.

In one embodiment, the *Plasmodium* antigen sequence and the matrix protein sequence are inserted into the MVA vector in a natural deletion site, a modified natural deletion site, or between essential or non-essential MVA genes.

In another embodiment, the *Plasmodium* antigen sequence and the matrix protein sequence are inserted into the same natural deletion site, a modified natural deletion site, or between the same essential or non-essential MVA genes.

In another embodiment, the *Plasmodium* antigen sequence is inserted into a deletion site selected from I, II, III, IV, V, or VI and the matrix protein sequence is inserted into a deletion site selected from I, II, III, IV, V, or VI.

In another embodiment, the *Plasmodium* antigen sequence and the matrix protein sequence are inserted into different natural deletion sites, different modified deletion sites, or between different essential or non-essential MVA genes.

In another embodiment, the *Plasmodium* antigen is inserted in a first deletion site and matrix protein sequence is inserted into a second deletion site.

In one embodiment, the *Plasmodium* antigen sequence and the matrix protein sequence are inserted into one or more deletion sites of the MVA vector.

In one embodiment, the matrix protein is selected from Marburg virus VP40 matrix protein, Ebola virus VP40 matrix protein, human immunodeficiency virus type 1 (HIV-1) matrix protein (Clade A, B or C), or Lassa virus matrix Z protein.

In one embodiment, the Ebola virus VP40 matrix protein is selected from Zaire Ebola virus VP40 or Sudan Ebola virus VP40.

In one embodiment, the *Plasmodium* antigen sequence and the matrix protein sequence are inserted into the MVA vector in a natural deletion site, a modified natural deletion site, or between essential or non-essential MVA genes.

In another embodiment, the *Plasmodium* antigen sequence and the matrix protein sequence are inserted into the same natural deletion site, a modified natural deletion site, or between the same essential or non-essential MVA genes.

In another embodiment, the *Plasmodium* antigen sequence is inserted into a deletion site selected from I, II, III, IV, V, or VI and the matrix protein sequence is inserted into a deletion site selected from I, II, III, IV, V, or VI.

In another embodiment, the *Plasmodium* antigen sequence and the matrix protein sequence are inserted into different natural deletion sites, different modified deletion sites, or between different essential or non-essential MVA genes.

In another embodiment, the *Plasmodium* antigen is inserted in a first deletion site and matrix protein sequence is inserted into a second deletion site.

In a particular embodiment, the *Plasmodium* antigen is inserted between two essential and highly conserved MVA genes; and the matrix protein sequence is inserted into a restructured and modified deletion III.

In a particular embodiment, the *Plasmodium* antigen sequence is inserted between two essential and highly conserved MVA genes to limit the formation of viable deletion mutants.

In a particular embodiment, the *Plasmodium* antigen protein sequence is inserted between MVA genes, 18R and G1L.

In a particular embodiment, the *Plasmodium* antigen protein sequence is inserted between MVA genes, A50R and B1R.

In a particular embodiment, the matrix protein sequence is inserted between MVA genes, 18R and G1L.

In a particular embodiment, the matrix protein sequence is inserted between MVA genes, A50R and B1R.

In one embodiment, the *Plasmodium* antigen protein sequence is expressed with a matrix protein sequence as a fusion protein.

In a particular embodiment, the *Plasmodium* antigen/matrix protein fusion protein sequence is inserted between MVA genes, 18R and G1L.

In a particular embodiment, the *Plasmodium* antigen/matrix protein fusion protein sequence is inserted between MVA genes, A50R and B1R.

In one embodiment, the promoter is selected from the group consisting of Pm2H5, Psyn II, and mH5 promoters, or combinations thereof.

In one embodiment, the recombinant MVA viral vector expresses a *Plasmodium* antigen and matrix proteins that assemble into VLPs.

In one embodiment, the deletion III site is restructured and modified to remove non-essential flanking sequences.

In one embodiment the *Plasmodium* antigen is CSP and the matrix protein is Zaire Ebola VP40, Sudan Ebola VP40, Marburg virus VP40, Lassa virus Z protein, or HIV Gag protein.

In one embodiment the *Plasmodium* antigen is MSP-1 and the matrix protein is Zaire Ebola VP40, Sudan Ebola VP40, Marburg virus VP40, Lassa virus Z protein, or HIV Gag protein.

In one embodiment the *Plasmodium* antigen is MSP-2 and the matrix protein is Zaire Ebola VP40, Sudan Ebola VP40, Marburg virus VP40, Lassa virus Z protein, or HIV Gag protein.

In one embodiment the *Plasmodium* antigen is MSP-3 and the matrix protein is Zaire Ebola VP40, Sudan Ebola VP40, Marburg virus VP40, Lassa virus Z protein, or HIV Gag protein.

In one embodiment the *Plasmodium* antigen is GLURP and the matrix protein is Zaire Ebola VP40, Sudan Ebola VP40, Marburg virus VP40, Lassa virus Z protein, or HIV Gag protein.

In one embodiment the *Plasmodium* antigen is EBA-175 and the matrix protein is Zaire Ebola VP40, Sudan Ebola VP40, Marburg virus VP40, Lassa virus Z protein, or HIV Gag protein.

In one embodiment the *Plasmodium* antigen is Pfs25 and the matrix protein is Zaire Ebola VP40, Sudan Ebola VP40, Marburg virus VP40, Lassa virus Z protein, or HIV Gag protein.

In one embodiment the *Plasmodium* antigen is Pfs230 and the matrix protein is Zaire Ebola VP40, Sudan Ebola VP40, Marburg virus VP40, Lassa virus Z protein, or HIV Gag protein.

In one embodiment the *Plasmodium* antigen is Pfs SEA-1 and the matrix protein is Zaire Ebola VP40, Sudan Ebola VP40, Marburg virus VP40, Lassa virus Z protein, or HIV Gag protein.

In one embodiment the *Plasmodium* antigen is Pfs45/48 and the matrix protein is Zaire Ebola VP40, Sudan Ebola VP40, Marburg virus VP40, Lassa virus Z protein, or HIV Gag protein.

In one embodiment the *Plasmodium* antigen is Pfs SEA-1 and the matrix protein is Zaire Ebola VP40, Sudan Ebola VP40, Marburg virus VP40, Lassa virus Z protein, or HIV Gag protein.

In one embodiment the *Plasmodium* antigen is CPBAg1 and the matrix protein is Zaire Ebola VP40, Sudan Ebola VP40, Marburg virus VP40, Lassa virus Z protein, or HIV Gag protein.

In one embodiment the *Plasmodium* antigen is AgAPN1 and the matrix protein is Zaire Ebola VP40, Sudan Ebola VP40, Marburg virus VP40, Lassa virus Z protein, or HIV Gag protein.

In one embodiment the *Plasmodium* antigen is SGS and the matrix protein is Zaire Ebola VP40, Sudan Ebola VP40, Marburg virus VP40, Lassa virus Z protein, or HIV Gag protein.

The one or more genes introduced into the recombinant viral vector are under the control of regulatory sequences that direct its expression in a cell.

The nucleic acid material of the viral vector may be encapsulated, e.g., in a lipid membrane or by structural proteins (e.g., capsid proteins), that may include one or more viral polypeptides.

In exemplary embodiments, the present invention is a recombinant viral vector (e.g., a recombinant MVA vector) comprising one or more genes, or one or more polypeptides encoded by the gene or genes, from a *Plasmodium* spp.

In one embodiment, the sequence encoding a *Plasmodium* antigen or immunogenic fragment thereof is inserted into deletion site I, II, III, IV, V, or VI of the MVA vector.

In one embodiment, the sequence encoding a *Plasmodium* antigen or immunogenic fragment thereof is inserted between 18R and G1L of the MVA vector, or into restructured and modified deletion III of the MVA vector; and a second sequence encoding a *Plasmodium* antigen or immunogenic fragment thereof is inserted between 18R and G1L of the MVA vector, or into restructured and modified deletion site III of the MVA vector.

In one embodiment, the recombinant vector comprises in a first deletion site, a nucleic acid sequence encoding a *Plasmodium* antigen or immunogenic fragment thereof operably linked to a promoter compatible with poxvirus expression systems, and in a second deletion site, a nucleic acid sequence encoding a VLP-forming protein operably linked to a promoter compatible with poxvirus expression systems.

In exemplary embodiments, the present invention is a recombinant MVA vector comprising at least one heterologous nucleic acid sequence (e.g., one or more sequences) encoding a *Plasmodium* antigen or immunogenic fragment thereof which is under the control of regulatory sequences that direct its expression in a cell. The sequence may be, for example, under the control of a promoter selected from the group consisting of Pm2H5, Psyn II, or mH5 promoters.

The recombinant viral vector of the present invention can be used to infect cells of a subject, which, in turn, promotes the translation into a protein product of the one or more heterologous sequence of the viral vector (e.g., a *Plasmodium* antigen or immunogenic fragment thereof). As discussed further herein, the recombinant viral vector can be administered to a subject so that it infects one or more cells of the subject, which then promotes expression of the one or more viral genes of the viral vector and stimulates an immune response that is therapeutic or protective against malaria.

In one embodiment, the recombinant MVA vaccine expresses proteins that assemble into virus-like particles (VLPs) comprising the *Plasmodium* antigen or immunogenic fragment thereof. While not wanting to be bound by any particular theory, it is believed that the *Plasmodium* antigen is provided to elicit a protective immune response and the matrix protein is provided to enable assembly of VLPs and as a target for T cell immune responses, thereby enhancing the protective immune response and providing cross-protection.

In one embodiment, the matrix protein is a Marburg virus matrix protein.

In one embodiment, the matrix protein is an Ebola virus matrix protein.

In one embodiment, the matrix protein is a Sudan virus matrix protein.

In one embodiment, the matrix protein is a human immunodeficiency virus type 1 (HIV-1) matrix protein.

In one embodiment, the matrix protein is a human immunodeficiency virus type 1 (HIV-1) matrix protein encoded by the gag gene.

In one embodiment, the matrix protein is a Lassa virus matrix protein.

In one embodiment, the matrix protein is a Lassa virus Z protein.

In one embodiment, the matrix protein is a fragment of a Lassa virus Z protein.

In one embodiment, the matrix protein is a matrix protein of a virus in the Filoviridae virus family.

In one embodiment, the matrix protein is a matrix protein of a virus in the Retroviridae virus family.

In one embodiment, the matrix protein is a matrix protein of a virus in the Arenaviridae virus family.

In one embodiment, the matrix protein is a matrix protein of a virus in the Flaviviridae virus family.

One or more nucleic acid sequences may be optimized for use in an MVA vector.

Optimization includes codon optimization, which employs silent mutations to change selected codons from the native sequences into synonymous codons that are optimally expressed by the host-vector system. Other types of optimization include the use of silent mutations to interrupt homopolymer stretches or transcription terminator motifs. Each of these optimization strategies can improve the stability of the gene, improve the stability of the transcript, or improve the level of protein expression from the sequence. In exemplary embodiments, the number of homopolymer stretches in the *Plasmodium* antigen sequence will be reduced to stabilize the construct. A silent mutation may be provided for anything similar to a vaccinia termination signal. An extra nucleotide may be added in order to express the transmembrane, rather than the secreted, form of any *Plasmodium* antigen.

In exemplary embodiments, the sequences are codon optimized for expression in MVA; sequences with runs of ≥5 deoxyguanosines, ≥5 deoxycytidines, ≥5 deoxyadenosines, and ≥5 deoxythymidines are interrupted by silent mutation to minimize loss of expression due to frame shift mutations; and the GP sequence is modified through addition of an extra nucleotide to express the transmembrane, rather than the secreted, form of the protein.

In one embodiment, the present invention provides a vaccine vector composition that is monovalent. As used herein the term monovalent refers to a vaccine vector composition that contains sequences from one *Plasmodium* antigen.

In another embodiment, the present invention provides a vaccine that is bivalent. As used herein the term bivalent refers to a vaccine vector composition that contains two vectors having sequences from different *Plasmodium* antigens.

In another embodiment, the present invention provides a vaccine that is trivalent. As used herein the term trivalent refers to a vaccine vector composition that contains three vectors having sequences from different *Plasmodium* antigens.

In another embodiment, the present invention provides a vaccine that is quadrivalent. As used herein the term quadrivalent refers to a vaccine vector composition that contains four vectors having sequences from different *Plasmodium* antigens. As used herein, the terms tetravalent and quadrivalent are synonymous.

The present invention also extends to host cells comprising the recombinant viral vector described above, as well as isolated virions prepared from host cells infected with the recombinant viral vector.

IV. Pharmaceutical Composition

The recombinant viral vectors or immunogenic peptides described herein are readily formulated as pharmaceutical compositions for veterinary or human use, either alone or in combination. The pharmaceutical composition may comprise a pharmaceutically acceptable diluent, excipient, carrier, or adjuvant.

In one embodiment, the present invention is a vaccine effective to protect and/or treat malaria comprising a recombinant MVA vector that expresses at least one *Plasmodium* antigen (e.g., a *Plasmodium* antigen) or an immunogenic fragment thereof. The vaccine composition may comprise one or more additional therapeutic agents.

The pharmaceutical composition may comprise 1, 2, 3, 4 or more than 4 different recombinant MVA vectors described herein.

In one embodiment, the present invention provides a vaccine vector composition that is monovalent. As used herein the term monovalent refers to a vaccine vector composition that contains one *Plasmodium* antigen.

In another embodiment, the present invention provides a vaccine that is bivalent. As used herein the term bivalent refers to a vaccine vector composition that contains two vectors having sequences from different *Plasmodium* antigens.

In another embodiment, the present invention provides a vaccine that is trivalent. As used herein the term trivalent refers to a vaccine vector composition that contains three vectors having sequences from different *Plasmodium* antigens.

In another embodiment, the present invention provides a vaccine that is quadrivalent. As used herein the term quadrivalent refers to a vaccine vector composition that contains four vectors having sequences from different *Plasmodium* antigens. As used herein, the terms tetravalent and quadrivalent are synonymous.

As used herein, the phrase "pharmaceutically acceptable carrier" encompasses any of the standard pharmaceutical carriers, such as those suitable for parenteral administration, such as, for example, by intramuscular, intraarticular (in the joints), intravenous, intradermal, intraperitoneal, and subcutaneous routes. Examples of such formulations include aqueous and non-aqueous, isotonic sterile injection solutions, which contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. One exemplary pharmaceutically acceptable carrier is physiological saline. Other physiologically acceptable diluents, excipients, carriers, or adjuvants and their formulations are known to those skilled in the art.

In one embodiments, adjuvants are used as immune response enhancers. In various embodiments, the immune response enhancer is selected from the group consisting of alum-based adjuvants, oil based adjuvants, Specol, RIBI, TiterMax, Montanide 1SA50 or Montanide ISA 720, GM-CSF, nonionic block copolymer-based adjuvants, dimethyl dioctadecyl ammoniumbromide (DDA) based adjuvants AS-1, AS-2, Ribi Adjuvant system based adjuvants, QS21, Quil A, SAF (Syntex adjuvant in its microfluidized form (SAF-m), dimethyl-dioctadecyl ammonium bromide (DDA), human complement based adjuvants m. vaccae, ISCOMS, MF-59, SBAS-2, SBAS-4, Enhanzyn®, RC-529, AGPs, MPL-SE, QS7, Escin; Digitonin; and *Gypsophila*, *Chenopodium quinoa* saponins.

The compositions utilized in the methods described herein can be administered by a route selected from, e.g., parenteral, intramuscular, intraarterial, intravascular, intravenous, intraperitoneal, subcutaneous, dermal, transdermal, ocular, inhalation, buccal, sublingual, perilingual, nasal, topical administration, and oral administration. The preferred method of administration can vary depending on various factors (e.g., the components of the composition being administered and the severity of the condition being treated). Formulations suitable for oral administration may consist of liquid solutions, such as an effective amount of the composition dissolved in a diluent (e.g., water, saline, or PEG-400), capsules, sachets or tablets, each containing a predetermined amount of the vaccine. The pharmaceutical composition may also be an aerosol formulation for inhalation, e.g., to the bronchial passageways. Aerosol formulations may be mixed with pressurized, pharmaceutically acceptable propellants (e.g., dichlorodifluoromethane, propane, or nitrogen).

For the purposes of this invention, pharmaceutical compositions suitable for delivering a therapeutic or biologically active agent can include, e.g., tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of these formulations can be prepared by well-known and accepted methods of art. See, for example, Remington: The Science and Practice of Pharmacy ($21^{st}$ ed.), ed. A R. Gennaro, Lippincott Williams & Wilkins, 2005, and Encyclopedia of Pharmaceutical Technology, ed. J. Swarbrick, Informa Healthcare, 2006, each of which is hereby incorporated by reference.

The immunogenicity of the composition (e.g., vaccine) may be significantly improved if the composition of the present invention is co-administered with an immunostimulatory agent or adjuvant. Suitable adjuvants well-known to those skilled in the art include, e.g., aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM-Matrix, DC-Chol, DDA, cytokines, and other adjuvants and derivatives thereof.

Pharmaceutical compositions according to the invention described herein may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastrointestinal tract; or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

Formulations suitable for oral administration can consist of (a) liquid solutions, such as an effective amount of the vaccine dissolved in diluents, such as water, saline or PEG 400; (b) capsules, sachets or tablets, each containing a predetermined amount of the vaccine, as liquids, solids, granules or gelatin; (c) suspensions in an appropriate liquid; (d) suitable emulsions; and (e) polysaccharide polymers such as chitins. The vaccine, alone or in combination with other suitable components, may also be made into aerosol formulations to be administered via inhalation, e.g., to the bronchial passageways. Aerosol formulations can be placed into pressurized acceptable propellants, such as dichlorodifluoromethane, propane, nitrogen, and the like.

Suitable formulations for rectal administration include, for example, suppositories, which consist of the vaccine with a suppository base. Suitable suppository bases include natural or synthetic triglycerides or paraffin hydrocarbons. In addition, it is also possible to use gelatin rectal capsules which consist of a combination of the vaccine with a base, including, for example, liquid triglycerides, polyethylene glycols, and paraffin hydrocarbons.

The vaccines of the present invention may also be co-administered with cytokines to further enhance immunogenicity. The cytokines may be administered by methods known to those skilled in the art, e.g., as a nucleic acid molecule in plasmid form or as a protein or fusion protein.

This invention also provides kits comprising the vaccines of the present invention. For example, kits comprising a vaccine and instructions for use are within the scope of this invention.

V. Method of Use

The compositions of the invention can be used as vaccines for inducing an immune response to a *Plasmodium* antigen.

In exemplary embodiments, the present invention provides a method of inducing an immune response to a *Plasmodium* antigen in a subject in need thereof, said method comprising administering a recombinant viral vector that encodes at least one *Plasmodium* antigen or immunogenic fragment thereof to the subject in an effective amount to generate an immune response to a *Plasmodium* antigen. The result of the method is that the subject is partially or completely immunized against the *Plasmodium* antigen.

In one embodiment, invention provides methods for activating an immune response in a subject using the compositions described herein. In some embodiments, the invention provides methods for promoting an immune response in a subject using a composition described herein. In some embodiments, the invention provides methods for increasing an immune response in a subject using a composition described herein. In some embodiments, the invention provides methods for enhancing an immune response in a subject using a composition described herein.

In exemplary embodiments, the present invention provides a method of treating, reducing, preventing or delaying malaria in a subject in need thereof, said method comprising administering the composition of the present invention to the subject in a therapeutically effective amount a recombinant MVA described herein. The result of treatment is a subject that has an improved therapeutic profile for malaria.

In exemplary embodiments, the present invention provides a method of treating malaria in a subject in need thereof, said method comprising administering the composition of the present invention to the subject in a therapeutically effective amount. The result of treatment is a subject that has an improved therapeutic profile for malaria.

In one embodiment, the immune response is a humoral immune response, a cellular immune response or a combination thereof.

In a particular embodiment, the immune response comprises production of binding antibodies against the *Plasmodium* antigen.

In a particular embodiment, the immune response comprises production of neutralizing antibodies against the *Plasmodium* antigen.

In a particular embodiment, the immune response comprises production of non-neutralizing antibodies against the *Plasmodium* antigen.

In a particular embodiment, the immune response comprises production of a cell-mediated immune response against the *Plasmodium* antigen.

In a particular embodiment, the immune response comprises production of neutralizing and non-neutralizing antibodies against the *Plasmodium* antigen. In a particular embodiment, the immune response comprises production of neutralizing antibodies and cell-mediated immunity against the *Plasmodium* antigen.

In a particular embodiment, the immune response comprises production of non-neutralizing antibodies and cell-mediated immunity against the *Plasmodium* antigen.

In a particular embodiment, the immune response comprises production of neutralizing antibodies, non-neutralizing antibodies, and cell-mediated immunity against the *Plasmodium* antigen.

In certain embodiments, the compositions of the invention can be used as vaccines for treating a subject at risk of developing malaria, or a subject already having malaria. The recombinant viral vector comprises genes or sequences encoding *Plasmodium* antigens, viral proteins to promote assembly of virus-like particles (VLPs) or additional enzymes to facilitate expression and glycosylation of the *Plasmodium* antigen.

Typically, the vaccines will be in an admixture and administered simultaneously, but may also be administered separately.

A subject to be treated according to the methods described herein may be one who has been diagnosed by a medical practitioner as having such a condition. (e.g., a subject having malaria). Diagnosis may be performed by any suitable means. One skilled in the art will understand that a subject to be treated according to the present invention may have been identified using standard tests or may have been identified, without examination, as one at high risk due to the presence of one or more risk factors.

Prophylactic treatment may be administered, for example, to a subject not yet having malaria but who is susceptible to, or otherwise at risk of developing malaria.

Therapeutic treatment may be administered, for example, to a subject already having malaria in order to improve or stabilize the subject's condition. The result is an improved therapeutic profile. In some instances, as compared with an equivalent untreated control, treatment may ameliorate a disorder or a symptom thereof by, e.g., 5%, 10%, 20%, 30%, 40%, 50%, 60%, 70%, 80%, 90%, 95%, or 100% as measured by any standard technique.

In other embodiments, treatment may result in amelioration of one or more symptoms of malaria. According to this embodiment, confirmation of treatment can be assessed by detecting an improvement in or the absence of symptoms.

In one embodiment, the present invention is a method of inducing an immune response in a subject (e.g., a human) by administering to the subject a recombinant viral vector that encodes at least one *Plasmodium* antigen or immunogenic fragment thereof. The immune response may be a cellular immune response or a humeral immune response, or a combination thereof.

The composition may be administered, e.g., by injection (e.g., intramuscular, intraarterial, intravascular, intravenous, intraperitoneal, or subcutaneous). It will be appreciated that more than one route of administering the vaccines of the present invention may be employed either simultaneously or sequentially (e.g., boosting). In addition, the vaccines of the present invention may be employed in combination with traditional immunization approaches such as employing protein antigens, vaccinia virus and inactivated virus, as vaccines. Thus, in one embodiment, the vaccines of the present invention are administered to a subject (the subject is "primed" with a vaccine of the present invention) and then a traditional vaccine is administered (the subject is "boosted" with a traditional vaccine). In another embodiment, a traditional vaccine is first administered to the subject followed by administration of a vaccine of the present invention. In yet another embodiment, a traditional vaccine and a vaccine of the present invention are co-administered.

While not to be bound by any specific mechanism, it is believed that upon inoculation with a pharmaceutical composition as described herein, the immune system of the host responds to the vaccine by producing antibodies, both secretory and serum, specific for one or more *Plasmodium* antigen or immunogenic fragments thereof; and by producing a cell-mediated immune response specific for one or more *Plasmodium* antigen or immunogenic fragments thereof. As a result of the vaccination, the host becomes at least partially or completely immune to one or more *Plasmodium* antigen or immunogenic fragments thereof, or resistant to developing moderate or severe diseases caused by malaria.

In one aspect, methods are provided to alleviate, reduce the severity of, or reduce the occurrence of, one or more of the symptoms associated with malaria comprising administering an effective amount of a pharmaceutical composition comprising a recombinant MVA viral vector that comprises *Plasmodium* antigen and matrix protein sequences optionally co-expressing sequences that facilitate expression of and desired glycosylation the *Plasmodium* antigen.

In another aspect, the invention provides methods of providing anti-*Plasmodium* antigen immunity comprising administering an effective amount of a pharmaceutical composition comprising a recombinant MVA vaccine expressing *Plasmodium* antigen and a viral matrix protein to permit the formation of VLPs.

It will also be appreciated that single or multiple administrations of the vaccine compositions of the present invention may be carried out. For example, subjects who are at particularly high risk of malaria may require multiple immunizations to establish and/or maintain protective immune responses. Levels of induced immunity can be monitored by measuring amounts of binding and neutralizing secretory and serum antibodies as well as levels of T cells, and dosages adjusted or vaccinations repeated as necessary to maintain desired levels of protection.

In one embodiment, administration is repeated at least twice, at least 3 times, at least 4 times, at least 5 times, at least 6 times, at least 7 times, at least 8 times, or more than 8 times.

In one embodiment, administration is repeated twice.

In one embodiment, about 2-8, about 4-8, or about 6-8 administrations are provided.

In one embodiment, about 1-4-week, 2-4 week, 3-4 week, 1 week, 2 week, 3 week, 4 week, or more than 4 week intervals are provided between administrations.

In one specific embodiment, a 4-week interval is used between 2 administrations. In one embodiment, the invention provides a method of monitoring treatment progress. In exemplary embodiments, the monitoring is focused on biological activity, immune response, and/or clinical response.

In one embodiment, the biological activity is a T-cell immune response, regulatory T-cell activity, or molecule response (MRD).

In one embodiment, immune response is monitored for example, by an immune assay such as a cytotoxicity assay, an intracellular cytokine assay, a tetramer assay, or an ELISPOT assay.

In one embodiment, upon improvement of a subject's condition (e.g., a change (e.g., decrease) in the level of disease in the subject), a maintenance dose of a compound, composition, or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

A. Dosage

The vaccines are administered in a manner compatible with the dosage formulation, and in such amount as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner and may be monitored on a patient-by-patient basis. However, suitable dosage ranges are readily determinable by one skilled in the art and generally range from about $5.0 \times 10^6$ $TCID_{50}$ to about $5.0 \times 10^9$ $TCID_{50}$. The dosage may also depend, without limitation, on the route of administration, the patient's state of health and weight, and the nature of the formulation.

The pharmaceutical compositions of the invention are administered in such an amount as will be therapeutically effective, immunogenic, and/or protective against a *Plasmodium* antigen. The dosage administered depends on the subject to be treated (e.g., the manner of administration and the age, body weight, capacity of the immune system, and general health of the subject being treated). The composition is administered in an amount to provide a sufficient level of expression that elicits an immune response without undue adverse physiological effects. Preferably, the composition of the invention is a heterologous viral vector that includes one or *Plasmodium* antigens or immunogenic fragments thereof and large matrix protein; and is administered at a dosage of, e.g., between $1.0 \times 10^4$ and $9.9 \times 10^{12}$ $TCID_{50}$ of the viral vector, preferably between $1.0 \times 10^5$ $TCID_{50}$ and $1.0 \times 10^{11}$ $TCID_{50}$ pfu, more preferably between $1.0 \times 10^6$ and $1.0 \times 10^{10}$ $TCID_{50}$ pfu, or most preferably between $5.0 \times 10^6$ and $5.0 \times 10^9$ $TCID_{50}$. The composition may include, e.g., at least $5.0 \times 10^6$ $TCID_{50}$ of the viral vector (e.g., $1.0 \times 10^8$ $TCID_{50}$ of the viral vector). A physician or researcher can decide the appropriate amount and dosage regimen.

The composition of the method may include, e.g., between $1.0 \times 10^4$ and $9.9 \times 10^{12}$ $TCID_{50}$ of the viral vector, preferably between $1.0 \times 10^5$ $TCID_{50}$ and $1.0 \times 10^{11}$ $TCID_{50}$ pfu, more preferably between $1.0 \times 10^6$ and $1.0 \times 10^{10}$ $TCID_{50}$ pfu, or most preferably between $5.0 \times 10^6$ and $5.0 \times 10^9$ $TCID_{50}$. The composition may include, e.g., at least $5.0 \times 10^6$ $TCID_{50}$ of the viral vector (e.g., $1.0 \times 10^8$ $TCID_{50}$ of the viral vector). The method may include, e.g., administering the composition to the subject two or more times.

The term "effective amount" is meant the amount of a composition administered to improve, inhibit, or ameliorate a condition of a subject, or a symptom of a disorder, in a clinically relevant manner (e.g., improve, inhibit, or ameliorate disease associated with malaria or provide an effective immune response to a *Plasmodium* antigen). Any improvement in the subject is considered sufficient to achieve treatment. Preferably, an amount sufficient to treat is an amount that prevents the occurrence or one or more symptoms of disease associated with malaria or is an amount that reduces the severity of, or the length of time during which a subject suffers from, one or more symptoms of malaria (e.g., by at least 10%, 20%, or 30%, more preferably by at least 50%, 60%, or 70%, and most preferably by at least 80%, 90%, 95%, 99%, or more, relative to a control subject that is not treated with a composition of the invention). A sufficient amount of the pharmaceutical composition used to practice the methods described herein (e.g., the prevention or treatment of malaria) varies depending upon the manner of administration and the age, body weight, and general health of the subject being treated.

It is important to note that the value of the present invention may never be demonstrated in terms of actual clinical benefit. Instead, it is likely that the value of the invention will be demonstrated in terms of success against a surrogate marker for protection. For an indication such as malaria, in which it is impractical or unethical to attempt to measure clinical benefit of an intervention, the FDA's Accelerated Approval process allows approval of a new vaccine based on efficacy against a surrogate endpoint. Therefore, the value of the invention may lie in its ability to induce an immune response that constitutes a surrogate marker for protection.

Similarly, FDA may allow approval of vaccines against *Plasmodium* antigens based on its Animal Rule. In this case, approval is achieved based on efficacy in animals.

The composition of the method may include, e.g., between $1.0 \times 10^4$ and $9.9 \times 10^{12}$ $TCID_{50}$ of the viral vector, preferably between $1.0 \times 10^5$ $TCID_{50}$ and $1.0 \times 10^{11}$ $TCID_{50}$ pfu, more preferably between $1.0 \times 10^6$ and $1.0 \times 10^{10}$ $TCID_{50}$ pfu, or most preferably between $5.0 \times 10^6$ and $5.0 \times 10^9$ $TCID_{50}$. The composition may include, e.g., at least $5.0 \times 10^6$ $TCID_{50}$ of the viral vector (e.g., $1.0 \times 10^8$ $TCID_{50}$ of the viral vector). The method may include, e.g., administering the composition two or more times.

In some instances it may be desirable to combine the *Plasmodium* antigen vaccines of the present invention with vaccines which induce protective responses to other agents, particularly other *Plasmodium* antigens. For example, the vaccine compositions of the present invention can be administered simultaneously, separately or sequentially with other genetic immunization vaccines such as those for influenza (Ulmer, J. B. et al., Science 259:1745-1749 (1993); Raz, E. et al., PNAS (USA) 91:9519-9523 (1994)), malaria (Doolan, D. L. et al., J. Exp. Med. 183:1739-1746 (1996); Sedegah, M. et al., PNAS (USA) 91:9866-9870 (1994)), and tuberculosis (Tascon, R. C. et al., Nat. Med. 2:888-892 (1996)).

B. Administration

As used herein, the term "administering" refers to a method of giving a dosage of a pharmaceutical composition of the invention to a subject. The compositions utilized in the methods described herein can be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, intraarterial, intravascular, and intramuscular administration. The preferred method of administration can vary depending on various factors (e.g., the components of the composition being administered, and the severity of the condition being treated).

Administration of the pharmaceutical compositions (e.g., vaccines) of the present invention can be by any of the routes known to one of skill in the art. Administration may be by, e.g., intramuscular injection. The compositions utilized in the methods described herein can also be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, and intramuscular administration. The preferred method of administration can vary depending on various factors, e.g., the components of the composition being administered, and the severity of the condition being treated.

In addition, single or multiple administrations of the compositions of the present invention may be given to a subject. For example, subjects who are particularly susceptible to developing malaria may require multiple treatments to establish and/or maintain protection against a *Plasmodium* antigen. Levels of induced immunity provided by the pharmaceutical compositions described herein can be monitored by, e.g., measuring amounts of neutralizing secretory and serum antibodies. The dosages may then be adjusted or repeated as necessary to maintain desired levels of protection against malaria or to reduce symptoms of malaria.

Increased vaccination efficacy can be obtained by timing the administration of the vector. Any of the priming and boosting compositions described above are suitable for use with the methods described here.

In one embodiment, MVA vectors are used for both priming and boosting purposes. Such protocols include but are not limited to MM, MMM, and MMMM.

In some embodiments, one, two, three, four, five, six, seven, eight, nine, ten, or more than ten MVA boosts are administered.

Vectors can be administered alone (i.e., a plasmid can be administered on one or several occasions with or without an alternative type of vaccine formulation (e.g., with or without administration of protein or another type of vector, such as a viral vector) and, optionally, with an adjuvant or in conjunction with (e.g., prior to) an alternative booster immunization (e.g., a live-vectored vaccine such as a recombinant modified vaccinia Ankara vector (MVA)) comprising an insert that may be distinct from that of the "prime" portion of the immunization or may be a related vaccine insert(s). For example, GM-CSF or other adjuvants known to those of skill in the art. The adjuvant can be a "genetic adjuvant" (i.e., a protein delivered by way of a DNA sequence).

In exemplary embodiments, the present invention is an immunization method comprising (i) administering a priming composition comprising a DNA plasmid comprising one or more sequences encoding a *Plasmodium* antigen or immunogenic fragment thereof; (ii) administering a first dose of a boosting composition comprising a modified vaccinia Ankara viral vector comprising one or more genes encoding a *Plasmodium* antigen or immunogenic fragment thereof; and (iii) administering a second dose of a boosting composition between about 12 and 20 weeks after the first dose, more particularly between about 14 and about 18 weeks after the first dose, even more particularly, about 16 weeks after the first dose.

In a particular embodiment, the *Plasmodium* antigens are the same in step (i)-(iii). Optionally, the method further comprises one or more additional steps, including, for example, the administration of one or more additional doses of the priming composition or a different priming composition (i.e., a second priming composition) and/or one or more additional doses of the boosting composition or a different boosting composition (i.e., a second boosting composition).

The claimed invention is further described by way of the following non-limiting examples. Further aspects and embodiments of the present invention will be apparent to those of ordinary skill in the art, in view of the above disclosure and following experimental exemplification, included by way of illustration and not limitation, and with reference to the attached figures.

EXAMPLES

Example 1. Generating an Immune Response to CSP Using MVA Vectors Expressing CSP-VLPs Overview Swiss mice were vaccinated with one of four constructs (N=5 per group) that contained CSP with 21 NANP-repeats (CSP21R) or a truncated CSP that had no repeats (CSPNR):
1. MVA-CSP21R
2. MVA-CSPNR
3. MVA-VP40 m.CSPNR
4. MVA-Gag.CSPNR Methods Sera were tested by ELISA against the following antigens: recombinant full length CSP (Genova), (NANP) 15 peptide (Life Tein), and truncated CSP lacking the central repeat region (N+C, in-house). Samples were tested in duplicate, and corrected for background reactivity.

Results

Sera from all vaccine groups (N=20) were tested between 1/100-1/64000 dilution for anti-CSP IgG. Only group 3 (MVA-CSP) 21R had detectable reactivity against full length CSP, which was relatively comparable to control mice vaccinated with recombinant CSP+Alum (FIG. 1). IgG-reactivity was measured to a peptide representative of the central NANP repeat region of CSP. Again, strong reactivity was only detected in mouse serum of MVA-CSP21R, and in control mice vaccinated with recombinant CSP.

A truncated CSP construct was expressed that contains the flanking regions of CSP only, termed N+C. To confirm this construct did not contain the central repeat region, it was tested using mouse anti-NANP MAbs against CSP-N+C, as well as full 25 length CSP and NANP-peptide as controls (FIG. 2). Two antibody clones (2H8 and 3C1) demonstrated strong IgG-reactivity to full-length CSP and a NANP repeat polymer, but not against CSP-N+C. Furthermore, rabbits were vaccinated with the CSP-N+C and tested the purified polyclonal rabbit anti-N+C IgG by ELISA. A strong signal was observed to full length CSP and CSP-N+C, but not to the NANP peptide. Taken together, these data confirm the truncated N+C construct does not contain the central NANP repeat region. Therefore group 3 was vaccinated with CSP21R. To confirm that the CSP21R construct generates high levels of antibodies, repeat immunizations of mice are performed with this construct together with a new construct, VP40-CSP21R.

Given that only the mice vaccinated with CSP21R had detectable IgG responses, this group was further tested for IgG subclass reactivity to CSP at 1/1000 dilution (FIG. 4). There were high levels IgG1, and variable levels of IgG2a, IgG2b and IgG3. The MVA-vaccinated mice showed a more favourable IgG subclass profile with a greater ratio of IgG2a, 2b, and IgG3 compared to IgG1, whereas CSP+Alum was strongly IgG1 skewed.

Sera were then tested for the ability to fix human complement using our recently optimised assays (Kurtovic L. et al, BMC Medicine 2018), and the ability to interact with human Fc-receptors, FcγRIIa and FcγRIIIa (FIG. 4).

Strong levels of C1q-fixation were observed, particularly by in sera from animal #25 that had low levels of IgG1 (which cannot activate complement) and the highest level of IgG2a, although low levels of IgG2b and IgG3. This was followed by sera from animal #24 that notably had very high levels of IgG2b and IgG3, and moderate IgG1. Strong FcγRIIa binding was only apparent in sera from animal #25, which also had the highest signal for FcγRIIIa binding although this was relatively low overall. It should be noted that human Fc-receptors were used in these assays, so the results should only be used to indicate potential activity. Further studies immunize rabbits to generate Abs for functional assays, as rabbit IgG is similar to human IgG1 and can fix human complement and bind human Fc-receptors.

Additional CSP-Based Vaccine
1. Immunize mice with VP40-CSP21R construct and compare with mice with initial VP40-CSP21R versus CSP21R construct
2. Repeat evaluation of IgG subclasses and functional activity with all mice
3. Evaluate Ab longevity (extend time-points)
4. Immunize rabbits to enable detailed studies of functional Ab activity
5. Perform prime-boost protocols with MVA and protein vaccines such as GSK CSP VLP or other VLPs or subunit proteins or fragments thereof
6. Test protection in a mouse model using genetically modified parasites that express Pf-CSP.

Example 2: Generating an Immune Response to Pfs-230 Using MVA Vectors Expressing Pfs-230-VLPs Overview Swiss mice are vaccinated with one of four constructs (N=5 per group) that contained Pfs-230:
1. MVA-Pfs230
2. MVA-VP40 m.Pfs230

Methods

Sera are tested by ELISA against the following antigens: recombinant full length Pfs230. Samples are tested in duplicate and corrected for background reactivity.

Results

Sera from all vaccine groups (N=20) are tested between 1/100-1/64000 dilution for anti-Pfs230 IgG.

Sera are then tested for the ability to fix human complement using recently optimised assays (Kurtovic L et al, BMC Medicine 2018), and the ability to interact with human Fc-receptors, FcγRIIa and FcγRIIIa (FIG. 4).

Immunization Studies
1. Immunize mice with VP40-Pfs230 vector construct
2. Repeat evaluation of IgG subclasses and functional activity with all mice
3. Evaluate Ab longevity (extend time-points)
4. Immunize rabbits to enable detailed studies of functional Ab activity
5. Perform prime-boost protocols with MVA and protein vaccines. MVA and protein (plus adjuvant) are administered at the same time in the same anatomical sites to generate an immune response in the same draining lymph nodes. Vector and or proteins are administered on Day 1 to prime and then on Day 28 to boost the primed immune response
6. Test protection in a mouse model using genetically modified parasites that express Pfs230

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are incorporated by reference in their entirety.

We claim:

1. A pharmaceutical composition comprising at least one recombinant modified vaccinia Ankara (MVA) viral vector and a pharmaceutically acceptable adjuvant, wherein the recombinant MVA viral vector comprises:
   i) a first nucleic acid sequence encoding a *Plasmodium falciparum* immunogenic polypeptide selected from the group consisting of circumsporozoite protein (CSP) and gametocyte surface protein P230 (Pfs230), the *Plasmodium falciparum* immunogenic polypeptide further comprising a transmembrane domain of a glycoprotein (GP) of Marburg virus; and
   ii) a second nucleic acid sequence encoding a Marburg virus VP40 matrix protein;
   wherein the CSP immunogenic polypeptide comprises the amino acid sequence of SEQ ID NO: 2, or an amino acid sequence at least 98% identical thereto;
   wherein the Pfs230 immunogenic polypeptide comprises the amino acid sequence of SEQ ID NO: 6, or an amino acid sequence at least 98% identical thereto;
   wherein the Marburg virus VP40 matrix protein comprises the amino acid sequence of SEQ ID NO: 8, or an amino acid sequence at least 98% identical thereto;
   wherein both the first nucleic acid and the second nucleic acid sequence are under the control of promoters compatible with poxvirus expression systems; and,
   wherein upon expression, the *Plasmodium falciparum* immunogenic polypeptide and Marburg virus VP40 matrix protein are capable of assembling together to form virus like particles (VLPs).

2. The pharmaceutical composition of claim 1, wherein the at least one recombinant MVA viral vector is formulated for intraperitoneal, intramuscular, intradermal, epidermal, mucosal, or intravenous administration.

3. The pharmaceutical composition of claim 1, wherein the adjuvant is an immune response enhancer.

4. The pharmaceutical composition of claim 1, wherein the first nucleic acid sequence is inserted between MVA genes 18R and G1L; and the second nucleic acid sequence is inserted into restructured and modified deletion site III between MVA genes A50R and B1R.

5. The pharmaceutical composition of claim 1, wherein the promoter is selected from the group consisting of Pm2H5, Psyn II, and mH5 promoters, and combinations thereof.

6. The pharmaceutical composition of claim 1, wherein the first nucleic acid and second nucleic acid sequence are optimized by one or more methods selected from the group consisting of: changing selected codons to other synonymous codons that are optimal for protein expression by MVA, interrupting homopolymer stretches using silent mutations, and interrupting transcription terminator motifs using silent mutations.

7. The pharmaceutical composition of claim 1, wherein the *Plasmodium falciparum* immunogenic polypeptide is CSP.

8. The pharmaceutical composition of claim 7, wherein the first nucleic acid sequence comprises the nucleic acid sequence of SEQ ID NO: 1.

9. The pharmaceutical composition of claim 7, wherein the second nucleic acid sequence comprises the nucleic acid sequence of SEQ ID NO: 7.

10. The pharmaceutical composition of claim 1, wherein the *Plasmodium falciparum* immunogenic polypeptide is Pfs230.

11. The pharmaceutical composition of claim 10, wherein the second nucleic acid sequence comprises the nucleic acid sequence of SEQ ID NO: 7.

12. A method of inducing an immune response in a subject in need thereof comprising administering an effective amount of the pharmaceutical composition of claim 1 to the subject.

13. The method of claim 12, wherein the immune response is selected from a humoral immune response, a cellular immune response, or a combination thereof.

14. The method of claim 12, wherein the immune response comprises (i) production of binding antibodies or neutralizing antibodies against the *Plasmodium* antigen, or (ii) production of non-neutralizing antibodies against the *Plasmodium* antigen.

15. The method of claim 12, wherein the immune response comprises production of a cell-mediated immune response against the *Plasmodium* antigen.

16. The method of claim 12, wherein the subject is a human.

17. The pharmaceutical composition of claim 1,
wherein the CSP immunogenic polypeptide comprises the amino acid sequence of SEQ ID NO: 2;
wherein the Pfs230 immunogenic polypeptide comprises the amino acid sequence of SEQ ID NO: 6; and,
wherein the Marburg virus VP40 matrix protein comprises the amino acid sequence of SEQ ID NO: 8.

* * * * *

SEQUENCE LISTING

```
Sequence total quantity: 11
SEQ ID NO: 1            moltype = DNA  length = 958
FEATURE                 Location/Qualifiers
source                  1..958
                        mol_type = other DNA
                        organism = Plasmodium falciparum
SEQUENCE: 1
atgatgagga agctagcgat cctatccgtg tcgtccttcc tattcgtcga ggcgctattc   60
caagagtacc agtgctatgg atcctcgtct aacaccagag tcctcaacga gctgaactac  120
gacaacgctg gaacgaacct atacaacgag ctagagatga actactacgg caagcaagag  180
aactggtaca gtctcaagaa gaactccaga tccttaggag agaacgacga tgggaacaac  240
gaggacaacg agaagctaag gaagccgaag cacaagaagc tgaagcaacc ggctgatggg  300
aatccagatc cgaatgcgaa tccgaatgta gatccgaacg ccaatcccaa cgtagatcca  360
aacgctaatc ctaatgttga tccgaacgcg aatcctaacg ccaatccgaa tgctaatccg  420
aacgcgaacc ctaatgctaa tcctaacgcg aatccgaatg ccaatccgaa cgcgaacccg  480
aatgctaatc cgaatgctaa tccgaacgcg aatccgaatg cgaatccgaa tgccaatcct  540
aatgcgaacc cgaacgccaa tccgaacgcg aatccgaacg ctaaccctaa cgttgatcct  600
aatgccaatc cgaacaagaa caatcaaggc aacggacaag gacacaacat gccgaatgat  660
ccgaacagga acgttgacga gaacgccaac gcgaactctg ccgtcaagaa caacaacaac  720
gaagaaccgt ccgacaagca catcaaggag tacctcaaca agatccagaa ctcactatcc  780
accgaatggt ctccatgttc tgtaacatgt gggaacggaa tccaagtcag aatcaagcct  840
```

```
ggatctgcga acaagccgaa ggatgaacta gattacgcga acgacatcga agaagaatc   900
tgcaagatgg agaagtgctc ctccgtgttc aacgtcgtca attcttaata attttat     958

SEQ ID NO: 2            moltype = AA  length = 315
FEATURE                 Location/Qualifiers
source                  1..315
                        mol_type = protein
                        organism = Plasmodium falciparum
SEQUENCE: 2
MMRKLAILSV SSFLFVEALF QEYQCYGSSS NTRVLNELNY DNAGTNLYNE LEMNYYGKQE   60
NWYSLKKNSR SLGENDDGNN EDNEKLRKPK HKKLKQPADG NPDPNANPNV DPNANPNVDP   120
NANPNVDPNA NPNANPNANP NANPNANPNA NPNANPNANP NANPNANPNA NPNANPNANP   180
NANPNANPNA NPNANPNVDP NANPNKNNQG NGQGHNMPND PNRNVDENAN ANSAVKNNNN   240
EEPSDKHIKE YLNKIQNSLS TEWSPCSVTC GNGIQVRIKG GSANKPKDEL DYANDIEKKI   300
CKMEKCSSVF NVVNS                                                    315

SEQ ID NO: 3            moltype = DNA  length = 670
FEATURE                 Location/Qualifiers
source                  1..670
                        mol_type = other DNA
                        organism = Plasmodium falciparum
SEQUENCE: 3
atgatgagga agctagcgat cctatccgtg tcgtccttcc tattcgtcga ggcgctattc   60
caagagtacc agtgctatgg atcctcgtct aacaccagag tcctcaacga gctgaactac   120
gacaacgctg gaacgaacct atacaacgag ctagagatga actactacgg caagcaagag   180
aactggtaca gtctcaagaa gaactccaga tccctcggag agaacgacga tggcaacaac   240
gaggacaacg agaagctaag gaagccgaag cacaagaagc tgaagcaacc ggctgatggg   300
aatccagatc caggtggtgg atccaacaag aacaatcaag gcaacggaca aggacacaac   360
atgccgaatg atccgaatag gaacgtagac gagaacgcga acgcgaactc tgccgtgaag   420
aacaacaaca acgaagaacc gtccgacaag cacatcaagg agtacctcaa caagatccag   480
aactctctat ccaccgaatg gtctccatgt tctgtaacat gtggaaacgg aatccaagtc   540
agaatcaagc caggatctgc gaacaagccg aaggatgaac tagattacgc gaacgacatc   600
gagaagaaga tctgcaagat ggagaagtgc ctccgtgt tcaacgtcgt caattcttaa   660
taattttat                                                            670

SEQ ID NO: 4            moltype = AA  length = 219
FEATURE                 Location/Qualifiers
source                  1..219
                        mol_type = protein
                        organism = Plasmodium falciparum
SEQUENCE: 4
MMRKLAILSV SSFLFVEALF QEYQCYGSSS NTRVLNELNY DNAGTNLYNE LEMNYYGKQE   60
NWYSLKKNSR SLGENDDGNN EDNEKLRKPK HKKLKQPADG NPDPGGSNK NNQGNGQGHN   120
MPNDPNRNVD ENANANSAVK NNNNEEPSDK HIKEYLNKIQ NSLSTEWSPC SVTCGNGIQV   180
RIKPGSANKP KDELDYANDI EKKICKMEKC SSVFNVVNS                          219

SEQ ID NO: 5            moltype = DNA  length = 670
FEATURE                 Location/Qualifiers
source                  1..670
                        mol_type = other DNA
                        organism = Plasmodium falciparum
SEQUENCE: 5
atgatgagga agctagcgat cctatccgtg tcgtccttcc tattcgtcga ggcgctattc   60
caagagtacc agtgctatgg atcctcgtct aacaccagag tcctcaacga gctgaactac   120
gacaacgctg gaacgaacct atacaacgag ctagagatga actactacgg caagcaagag   180
aactggtaca gtctcaagaa gaactccaga tccctcggag agaacgacga tggcaacaac   240
gaggacaacg agaagctaag gaagccgaag cacaagaagc tgaagcaacc ggctgatggg   300
aatccagatc caggtggtgg atccaacaag aacaatcaag gcaacggaca aggacacaac   360
atgccgaatg atccgaatag gaacgtagac gagaacgcga acgcgaactc tgccgtgaag   420
aacaacaaca acgaagaacc gtccgacaag cacatcaagg agtacctcaa caagatccag   480
aactctctat ccaccgaatg gtctccatgt tctgtaacat gtggaaacgg aatccaagtc   540
agaatcaagc caggatctgc gaacaagccg aaggatgaac tagattacgc gaacgacatc   600
gagaagaaga tctgcaagat ggagaagtgc ctccgtgt tcaacgtcgt caattcttaa   660
taattttat                                                            670

SEQ ID NO: 6            moltype = AA  length = 195
FEATURE                 Location/Qualifiers
source                  1..195
                        mol_type = protein
                        organism = Plasmodium falciparum
SEQUENCE: 6
SVLQSGALPS VGVDELDKID LSYETTESGD TAVSEDSYDK YASNNTNKEY VCDFTDQLKP   60
TESGPKVKKC EVKVNEPLIK VKIICPLKGS VEKLYDNIEY VPKKSPYVVL TKEETKLKEK   120
LLSKLIYGLL ISPTVNEKEN NFKEGVIEFT LPPVVHKATV FYFICDNSKT EDDNKKGNRG   180
IVEVYVEPYG NKING                                                    195

SEQ ID NO: 7            moltype = DNA  length = 915
FEATURE                 Location/Qualifiers
source                  1..915
```

|  |  | mol_type = other DNA |  |
|  |  | organism = Marburg virus |  |

SEQUENCE: 7
```
atggcgtcta gttctaatta taatacttat atgcaatatc taaatccacc accatatgcg   60
gatcatggtg ctaatcaact aattccagcg gatcaactat ctaatcaaca tggaattaca  120
ccaaattatg ttggagatct aaatctagat gatcagttta aaggaaatgt tgtcatgcg  180
tttacactag aagcgattat tgatatttct gcgtataatg aaagaacagt aaaaggtgta  240
ccagcttggc taccactagg aattatgtct aattttgaat atccactagc gcatacagta  300
gcggcgctat tgacaggatc ttatacaatt acacagttta cacataatgg acaaaagttt  360
gttagagtaa atagaccagg aactggaata ccagcgcatc cactaagaat gctaagagaa  420
ggaaatcaag ctttattca aaatatggtt attccaagaa atttctctac aaatcagttt  480
acttataatc taactaatct agtactatct gtacaaaagc taccagatga tgcttggaga  540
ccatctaaag ataaactaat tggaaataca atgcatccag cgatttctat tcatccaaat  600
ctaccaccaa tagtactacc aactgtaaag aacaagcgt atagacaaca taagaatcca  660
aataatggac cactattggc gatttctgga attctacatc aactaagagt agaaaagta  720
ccagaaaaga catctttgtt tagaatttct ctaccagcgg atatgttttc tgtaaaagaa  780
ggaatgatga agaaaagagg agaatcttct ccagtagtat atttcaagc gccagaaaat  840
tttccattga atggttttaa taatagacaa gtagtactag cgtatgcgaa tccaacacta  900
tctgcgatat aataa                                                   915
```

| SEQ ID NO: 8 | moltype = AA  length = 303 |
| FEATURE | Location/Qualifiers |
| source | 1..303 |
|  | mol_type = protein |
|  | organism = Marburg virus |

SEQUENCE: 8
```
MASSSNYNTY MQYLNPPPYA DHGANQLIPA DQLSNQHGIT PNYVGDLNLD DQFKGNVCHA   60
FTLEAIIDIS AYNERTVKGV PAWLPLGIMS NFEYPLAHTV AALLTGSYTI TQFTHNGQKF  120
VRVNRLGTGI PAHPLRMLRE GNQAFIQNMV IPRNFSTNQF TYNLTNLVLS VQKLPDDAWR  180
PSKDKLIGNT MHPAISIHPN LPPIVLPTVK KQAYRQHKNP NNGPLLAISG ILHQLRVEKV  240
PEKTSLFRIS LPADMFSVKE GMMKKRGESS PVVYFQAPEN FPLNGFNNRQ VVLAYANPTL  300
SAI                                                                303
```

| SEQ ID NO: 9 | moltype = DNA  length = 5807 |
| FEATURE | Location/Qualifiers |
| misc_feature | 1..5807 |
|  | note = Shuttle plasmid vector for VP40 |
| source | 1..5807 |
|  | mol_type = other DNA |
|  | organism = synthetic construct |

SEQUENCE: 9
```
gaattcggag tatacgaacc gggaaagaga agatggttaa aaataaagcg agactatttg   60
aacgaggggtt ccatgcaga ttctgccgat ttagtagtac taggtgctta ctatggtaaa  120
ggagcaaagg gtggtatcat ggcagtctttt ctaatgggtt gttacgacga tgaatccgt  180
aaatggaaga cggttaccaa gtgttcagga cacgatgata atacgttaag ggagttgcaa  240
gaccaattaa agatgattaa aattaacaag atcccaaaa aaattccaga gtggttagta  300
gttaataaaa tctatattcc cgattttgta gtagaggatc caaaacaatc tcagatatgg  360
gaaatttcag gagcagagtt tacatcttcc aagtcccata ccgcaaatgg aatatccatt  420
agatttccta gatttactag gataagagag gataaacgt ggaaagaatc tactcatcta  480
aacgatttag taaacttgac taaatcttaa tttttatggc gcgcctttca ttttgttttt  540
ttctatgcta taaatggtga gcaagggcga ggagctgttc accggggtgg tgcccatctt  600
ggtcgagctg gacggcgacg taaacggcca aagttcagc gtgtccggcg agggcgaggg  660
cgatgccacc tacggcaagc tgaccctgaa gttcatctgc accaccggca agctgcccgt  720
gccctggccc accctcgtga ccaccctgac ctacggcgtg cagtgcttca gccgctaccc  780
cgaccacatg aagcagcacg acttcttcaa gtccgccatg cccgaaggct acgtccagga  840
gcgcaccatc ttcttcaagg acgacggcaa ctacaagacc cgcgccgagg tgaagttcga  900
gggcgacacc ctggtgaacc gcatcgagct gaagggcatc gacttcaagg aggacggcaa  960
catcctgggg cacaagctgg agtacaacta caacagccac aacgtctata tcatggccga 1020
caagcagaag aacggcatca aggtgaactt caagatccgc cacaacatcg aggacggcag 1080
cgtgcagctc gccgaccact accagcagaa caccccatc ggcgacggcc ccgtgctgct 1140
gcccgacaac cactacctga gcacccagtc cgccctgagc aaagacccca acgagaagcg 1200
cgatcacatg gtcctgctgg agttcgtgac cgccgccggg atcactctcg gcatgcacga 1260
gctgtacaag taagagctcc ccgatttgt agtagaggat ccaaaacaat ctcagatatg 1320
ggaaatttca ggagcagagt ttacatcttc caagtcccat accgcaaatg gaatatccat 1380
tagatttcct agatttacta ggataagaga ggataaaacg tggaaagaat ctactcatct 1440
aaacgattta gtaaacttga ctaaatctta atttttatct cgaggccgct ggtacccaac 1500
ctaaaaattg aaaataaata caaggttct tgagggttgt gttaaattga aagcgagaaa 1560
taatcataaa taagcccggg atggcgtcta gttctaatta taatacttat atgcaatatc 1620
taaatccacc accatatgcg gatcatggtg ctaatcaact aattccagcg gatcaactat 1680
ctaatcaaca tggaattaca ccaaattatg ttggagatct aaatctagat gatcagttta 1740
aaggaaatgt tgtcatgcg tttacactag aagcgattat tgatatttct gcgtataatg 1800
aaagaacagt aaaaggtgta ccagcttggc taccactagg aattatgtct aattttgaat 1860
atccactagc gcatacagta gcggcgctat tgacaggatc ttatacaatt acacagttta 1920
cacataatgg acaaaagttt gttagagtaa atagaccagg aactggaata ccagcgcatc 1980
cactaagaat gctaagagaa ggaaatcaag ctttattca aaatatggtt attccaagaa 2040
atttctctac aaatcagttt acttataatc taactaatct agtactatct gtacaaaagc 2100
taccagatga tgcttggaga ccatctaaag ataaactaat tggaaataca atgcatccag 2160
cgatttctat tcatccaaat ctaccaccaa tagtactacc aactgtaaag aacaagcgt 2220
atagacaaca taagaatcca aataatggac cactattggc gatttctgga attctacatc 2280
```

-continued

```
aactaagagt agaaaaggta ccagaaaaga catctttgtt tagaatttct ctaccagcgg  2340
atatgttttc tgtaaaagaa ggaatgatga agaaaagagg agaatcttct ccagtagtat  2400
attttcaagc gccagaaaat tttccattga atggttttaa taatagacaa gtagtactag  2460
cgtatgcgaa tccaacacta tctgcgtat aataagtcga cctgcagcta atgtattagt  2520
taaatattaa aacttaccac gtaaaactta aaatttaaaa tgatatttca ttgacagata  2580
gatcacacat tatgaacttt caaggacttg tgttaactga caattgcaaa atcaatgggg  2640
tcgttggacc attaatagga aaggtggat ttggtagtat ttatactact aatgacaata  2700
attatgtagt aaaaatagag cccaaagcta acggatcatt atttaccgaa caggcatttt  2760
atactagagt acttaaacca tccgttatcg aagaatgaaa aaaatctcac aaatataaagc  2820
acgtaggtct tatccgtgc aaggcatttg gtctatacaa atccattaat gtggaatatc  2880
gattcttggt aattaataga ttaggtgcag atctagatgc ggtgatcaga gccaataata  2940
atagattacc aaaaaggtcg gtgatgttga tcggaatcga aatcttaaat accatacaat  3000
ttatgcacga gcaaggatat tctcacgag atattaaagc gagtaatata gtcttggatc  3060
aaatagataa gaataaatta tatctagtgg attacggatt ggtttctaaa ttcatgtcaa  3120
gcttgtctcc ctatagtgag tcgtattaga gcttggcgta atcatggtca tagctgtttc  3180
ctgtgtgaaa ttgttatccg ctcacaattc cacacaacat acgagccgga agcataaagt  3240
gtaaagcctg gggtgcctaa tgagtgagct aactcacatt aattgcgttg cgctcactgc  3300
ccgcttttcga gtcgggaaac ctgtcgtgcc agctgcatta atgaatcggc caacgcgcgg  3360
ggagaggcgg tttgcgtatt gggcgctctt ccgcttcctc gctcactgac tcgctgcgct  3420
cggtcgttcg gctgcggcga gcggtatcag ctcactcaaa ggcggtaata cggttatcca  3480
cagaatcagg ggataacgca ggaaagaaca tgtgagcaaa aggccagcaa aaggccagga  3540
accgtaaaaa ggccgcgttg ctggcgtttt tcgataggct ccgcccccct gacgagcatc  3600
acaaaaatcg acgctcaagt cagaggtggc gaaacccgac aggactataa agataccagg  3660
cgtttccccc tggaagctcc ctcgtgcgct ctcctgttcc gaccctgccg cttaccggat  3720
acctgtccgc ctttctccct tcgggaagcg tggcgctttc tcatagctca cgctgtaggt  3780
atctcagttc ggtgtaggtc gttcgctcca agctgggctg tgtgcacgaa ccccccgttc  3840
agcccgaccg ctgcgcctta tccggtaact atcgtcttga gtccaacccg gtaagacacg  3900
acttatcgcc actggcagca gccactggta acaggattag cagagcgagg tatgtaggcg  3960
gtgctacaga gttcttgaag tggtggccta actacggcta cactagaagg acagtatttg  4020
gtatctgcgc tctgctgaag ccagttacct tcggaaaaag agttggtagc tcttgatccg  4080
gcaaacaaac caccgctggt agcggtggtt tttttgtttg caagcagcag attacgcgca  4140
gaaaaaaagg atctcaagaa gatcctttga tcttttctac ggggtctgac gctcagtgga  4200
acgaaaactc acgttaaggg attttggtca tgagattatc aaaaaggatc ttcacctaga  4260
tccttttaaa ttaaaaatga gttttaaat caatcaatat tatatatgag taaacttggt  4320
ctgacagtta ccaatgctta atcagtgagg cacctatctc agcgatctgt ctatttcgtt  4380
catccatagt tgcctgactc cccgtcgtgt agataactac gatacgggag ggcttaccat  4440
ctggccccag tgctgcaatg ataccgcgag acccacgctc accggctcca gatttatcag  4500
caataaacca gccagccgga agggccgagc gcagaagtgg tcctgcaact ttatccgcct  4560
ccatccagtc tattaattgt tgccgggaag ctagagtaag tagttcgcca gttaatagtt  4620
tgcgcaacgt tgttggcatt gctacaggca tcgtggtgtc acgctcgtcg tttggtatgg  4680
cttcattcag ctccggttcc caacgatcaa ggcgagttac atgatccccc atgttgtgca  4740
aaaaagcggt tagctccttc ggtcctccga tcgttgtcag aagtaagttg gccgcagtgt  4800
tatcactcat ggttatgca gcactgcata attctcttac tgtcatgcca tccgtaagat  4860
gcttttctgt gactggtgag tactcaacca agtcattctg agaatagtgt atgcggcgac  4920
cgagttgctc ttgcccggcg tcaatacggg ataataccgc gccacatagc agaactttaa  4980
aagtgctcat cattggaaaa cgttcttcgg ggcgaaaact ctcaaggatc ttaccgctgt  5040
tgagatccag ttcgatgtaa cccactcgtg cacccaactg atcttcagca tcttttactt  5100
tcaccagcgt ttctgggtga gcaaaaacag gaaggcaaaa tgccgcaaaa aagggaataa  5160
gggcgacacg gaaatgttga atactcatac tcttcctttt tcaatattat tgaagcattt  5220
atcagggtta ttgtctcatg agcggataca tatttgaatg tatttagaaa aataaacaaa  5280
taggggttcc gcgcacattt ccccgaaaag tgccacctga cgtctaagaa accattatta  5340
tcatgacatt aacctataaa aataggcgta tcacgaggcc ctttcgtctc gcgcgtttcg  5400
gtgatgacgg tgaaaacctc tgacacatgc agctcccgga gacggtcaca gcttgtctgt  5460
aagcggatgc cgggagcaga caagcccgtc agggcgcgtc agcgggtgtt ggcgggtgtc  5520
ggggctggct taactatgcg gcatcagagc agattgtact gagagtgcac catatgcggt  5580
gtgaaatacc gcacagatgc gtaaggagaa aataccgcat caggcgccat tcgccattca  5640
ggctgcgcaa ctgttgggaa gggcgatcgg tgcgggcctc ttcgctatta cgccagctgg  5700
cgaaaggggg atgtgctgca aggcgattaa gttgggtaac gccagggttt tcccagtcac  5760
gacgttgtaa aacgacggcc agtgaattgg atttaggtga cactata             5807
```

```
SEQ ID NO: 10          moltype = DNA   length = 5991
FEATURE                Location/Qualifiers
misc_feature           1..5991
                       note = Shuttle plasmid vector for CSP21R
source                 1..5991
                       mol_type = other DNA
                       organism = synthetic construct
SEQUENCE: 10
gaattccctg ggacatacgt atatttctat gatctgtctt atatgaagtc tatacagcga   60
atagattcag aatttctaca taattatata ttgtacgcta ataagtttaa tctaacactc  120
cccgaagatt tgtttataat ccctacaaat ttggatattc tatggcgtac aaaggaatat  180
atagactcgt tcgatattag tacagaaaca tggaataaat tattatccaa ttattatatg  240
aagatgatag agtatgctaa actttatgta ctaagtccta ttctcgctga ggagttggat  300
aatttgaga ggacgggaga attaactagt attgtacaag aagccatttt atctctaaat  360
ttacgaatta agattttaaa ttttaaacat aaagatgatg atacgtatat acactttgt  420
aaaatatatt tcggtgtcta taacggaaca aacgctacta tatattatca tagacctcta  480
acgggatata tgaatatgat ttcagatact atatttgttc ctgtagataa taactaaggc  540
gcgcctttca tttttgttttt ttctatgcta taaatggtga gcaagggcga ggagctgttc  600
accggggtgg tgcccatcct ggtcgagctg gacggcgacg taaacggcca aagttcagc  660
```

```
gtgtccggcg agggcgaggg cgatgccacc tacggcaagc tgaccctgaa gttcatctgc  720
accaccggca agctgcccgt gccctggccc accctcgtga ccaccctgac ctacggcgtg  780
cagtgcttca gccgctaccc cgaccacatg aagcagcacg acttcttcaa gtccgccatg  840
cccgaaggct acgtccagga gcgcaccatc ttcttcaagg acgacggcaa ctacaagacc  900
cgcgcggagg tgaagttcga gggcgacacc ctggtgaacc gcatcgagct gaagggcatc  960
gacttcaagg aggacggcaa catcctgggg cacaagctgg agtacaacta caacagccac 1020
aacgtctata tcatggccga caagcagaag aacggcatca aggtgaactt caagatccgc 1080
cacaacatcg aggacggcag cgtgcagctc gccgaccact accagcagaa cacccccatc 1140
ggcgacggcc ccgtgctgct gcccgacaac cactacctga gcacccagtc cgccctgagc 1200
aaagacccca acgagaagcg cgatcacatg gtcctgctgg agttcgtgac cgccgccggg 1260
atcactctcg gcatgcacga gctgtacaag taagagctcg aggacgggag aattaactag 1320
tattgtacaa gaagccattt tatctctaaa tttacgaatt aagattttaa attttaaaca 1380
taaagatgat gatacgtata tacactttg taaaatatta ttcggtgtct ataacggaac 1440
aaacgctact atatattatc atagacctct aacgggatat atgaatatga tttcagatac 1500
tatatttgtt cctgtagata ataactaact cgaggccgct ggtacccaac ctaaaaattg 1560
aaaataaata caaggttct tgagggttgt gttaaattga aagcgagaaa taatcataaa 1620
taagcccggg atgatgagga agctagcgat cctatccgtg tcgtccttcc tattcgtcga 1680
ggcgctattc caagagtacc agtgctatgg atcctcgtct aacaccagag tcctcaacga 1740
gctgaactac gacaacgctg gaacgaacct atacaacgag ctagagatga actactacgg 1800
caagcaagag aactggtaca gtctcaagaa gaactccaga tccttaggag agaacgacga 1860
tgggaacaac gaggacaacg agaagctaag gaagccgaag cacaagaagc tgaagcaacc 1920
ggctgatggg aatccagatc cgaatgcgaa tccgaatgta gatccgaacg ccaatcccaa 1980
cgtagatcca aacgctaatc ctaatgttga tccgaacgcg aatcctaacg ccaatccgaa 2040
tgctaatccg aacgcgaacc ctaatgctaa tcctaacgcg aatccgaatg ccaatccgaa 2100
cgcgaacccg aatgctaatc cgaatgctaa tccgaacgcg aatccgaatg cgaatccgaa 2160
tgccaatcct aatgcgaacc cgaacgccaa tccgaacgcg aatccgacaa ctaaccctaa 2220
cgttgatcct aatgccaatc cgaacaagaa caatcaaggc aacggacaag acacaacat 2280
gccgaatgat ccgaacagga acgttgacga gaacgccaac gcgaactctg ccgtcaagaa 2340
caacaacaac gaagaaccgt ccgacaagca catcaaggag tacctcaaca agatccgaaa 2400
ctcactatcc accgaatggt ctccatgttc tgtaacatgt gggaacggaa tccaagtcag 2460
aatcaagcct ggatctgcga acaagccgaa ggatgaacta gattacgcga acgacatcga 2520
gaagaagatc tgcaagatgg agaagtgctc ctccgtgttc aacgtcgtca attcttaata 2580
atttttatgt cgacctgcag tcaaactcta atgaccacat cttttttag agatgaaaaa 2640
ttttccacat ctccttttgt agacacgact aaacattttg cagaaaaag tttattagtg 2700
tttagataat cgtatacttc atcagtgtag atagtaaatg tgaacagata aaaggtattc 2760
ttgctcaata gattggtaaa ttccatagaa tatattaatc ctttcttctt gagatcccac 2820
atcatttcaa ccagagacgt tttatccaat gatttacctc gtactatacc acatacaaaa 2880
ctagatttg cagtgacgtc gtatctggta ttcctaccaa acaaaatttt acttttagtt 2940
cttttagaaa attctaaggt agaatctcta tttgccaata tgtcatctat ggaattacca 3000
ctagcaaaaa atgatagaaa tatatattga tacatcgcag ctggttttga tctactatac 3060
tttaaaaacg aatcagattc cataattgcc tgtatatcat cagctgaaaa actatgtttt 3120
acacgtattc cttcggcatt tcttttaat gatatatctt gtttagacaa tgataaagtt 3180
atcatgtcca tgagagacgc gtctccgtat cgtataaata tttcattaga tgttagacgc 3240
ttcattaggg gtatacttct ataaggtttc ttaatcagtc catcattggt tgcgtcaaga 3300
acaagcttgt ctcccctatag tgagtcgtat tagagcttgg cgtaatcatg gtcatagctg 3360
tttcctgtgt gaaattgtta tccgctcaca attccacaca acatacgagc cggaagcata 3420
aagtgtaaag cctggggtgc ctaatgagtg agctaactca cattaattgc gttgcgctca 3480
ctgcccgctt tcgagtcggg aaacctgtcg tgccagctgc attaatgaat cggccaacgc 3540
gcggggagag gcggtttgcg tattgggcgc tcttccgctt cctcgctcac tgactcgctg 3600
cgctcggtcg ttcggctgcg gcgagcggta tcagctcact caaaggcggt aatacggtta 3660
tccacagaat caggggataa cgcaggaaag aacatgtgag caaaaggcca gcaaaaggcc 3720
aggaaccgta aaaaggccgc gttgctggcg tttttcgata ggctccgccc cctgacgag 3780
catcacaaaa atcgacgctc aagtcagagg tggcgaaacc cgacaggact ataaagatac 3840
caggcgtttc cccctggaag ctccctcgtg cgctctcctg ttccgaccct gccgcttacc 3900
ggatacctgt ccgcctttct cccttcggga agcgtggcgc tttctcatag ctcacgctgt 3960
aggtatctca gttcggtgta ggtcgttcgc tccaagctgg gctgtgtgca cgaaccccc 4020
gttcagcccg accgctgcgc cttatccggt aactatcgtc ttgagtccaa cccggtaaga 4080
cacgacttat cgccactggc agcagccact ggtaacagga ttagcagagc gaggtatgta 4140
ggcggtgcta cagagttctt gaagtggtgg cctaactacg gctacactag aaggacagta 4200
tttgtatct gcgctctgct gaagccagtt accttcggaa aaagagttgg tagctcttga 4260
tccggcaaac aaaccaccgc tggtagcggt ggtttttttg tttgcaagca gcagattacg 4320
cgcagaaaaa aaggatctca agaagatcct ttgatctttt ctacggggtc tgacgctcag 4380
tggaacgaaa actcacgtta agggattttg gtcatgagat tatcaaaaag gatcttcacc 4440
tagatccttt taattaaaaa atgaagtttt aaatcaactt aaagtatata tgagtaaact 4500
tggtctgaca gttaccaatg cttaatcagt gaggcaccta tctcagcgat ctgtctattt 4560
cgttcatcca tagttgcctg actccccgtc gtgtagataa ctacgatacg ggagggctta 4620
ccatctggcc ccagtgctgc aatgataccg cgagacccac gctcaccggc tccagattta 4680
tcagcaataa accagccagc cggaagggcc gagcgcagaa gtggtcctgc aactttatcc 4740
gcctccatcc agtctattaa ttgttgccgg gaagctagag taagtagttc gccagttaat 4800
agtttgcgca acgttgttgg cattgctaca ggcatcgtgg tgtcacgctc gtcgtttggt 4860
atggcttcat tcagctccgg ttcccaacga tcaaggcgag ttacatgatc cccatgttg 4920
tgcaaaaaag cggttagctc cttcggtcct ccgatcgttg tcagaagtaa gttggccgca 4980
gtgttatcac tcatggttat ggcagcactg cataattctc ttactgtcat gccatccgta 5040
agatgctttt ctgtgactgg tgagtactca accaagtcat tctgagaata gtgtatgcgg 5100
cgaccgagtt gctcttgccc ggcgtcaata cgggataata ccgcgccaca tagcagaact 5160
ttaaaagtgc tcatcattgg aaaacgttct cggggcgaa aactctcaag gatcttaccg 5220
ctgttgagat ccagttcgat gtaacccact cgtgcaccca actgatcttc agcatctttt 5280
actttcacca gcgtttctgg gtgagcaaaa acaggaaggc aaaatgccgc aaaaaaggga 5340
ataagggcga cacggaaatg ttgaatactc atactcttcc ttttcaata ttattgaagc 5400
```

```
atttatcagg gttattgtct catgagcgga tacatatttg aatgtattta gaaaaataaa   5460
caaatagggg ttccgcgcac atttccccga aaagtgccac ctgacgtcta agaaaccatt   5520
attatcatga cattaaccta taaaaatagg cgtatcacga ggccctttcg tctcgcgcgt   5580
ttcggtgatg acggtgaaaa cctctgacac atgcagctcc cggagacggt cacagcttgt   5640
ctgtaagcgg atgccgggag cagacaagcc cgtcagggcg cgtcagcggg tgttggcggg   5700
tgtcggggct ggcttaacta tgcggcatca gagcagatt tactgagagt gcaccatatg    5760
cggtgtgaaa taccgcacag atgcgtaagg agaaaatacc gcatcaggcg ccattcgcca   5820
ttcaggctgc gcaactgttg ggaagggcga tcggtgcggg cctcttcgct attacgccag   5880
ctggcgaaag ggggatgtgc tgcaaggcga ttaagttggg taacgccagg gttttcccag   5940
tcacgacgtt gtaaaacgac ggccagtgaa ttggatttag gtgacactat a            5991

SEQ ID NO: 11          moltype = DNA   length = 5703
FEATURE                Location/Qualifiers
misc_feature           1..5703
                       note = Shuttle plasmid vector for CSPNR
source                 1..5703
                       mol_type = other DNA
                       organism = synthetic construct
SEQUENCE: 11
gaattccctg ggacatacgt atatttctat gatctgtctt atatgaagtc tatacagcga     60
atagattcag aatttctaca taattatata ttgtacgcta ataagtttaa tctaacactc    120
cccgaagatt tgtttataat ccctacaaat ttggatattc tatggcgtac aaaggaatat    180
atagactcgt tcgatattag tacagaaaca tggaataaat tattatccaa ttattatatg    240
aagatgatag agtatgctaa actttatgta ctaagtccta ttctcgctga ggagttggat    300
aattttgaga ggacgggaga attaactagt attgtacaag aagccatttt atctctaaat    360
ttacgaatta agattttaaa ttttaaacat aaagatgata atacgtatat acactttgt    420
aaaatattat tcggtgtcta taacggaaca aacgctacta tatattatca tagacctcta    480
acgggatata tgaatatgat ttcagatact atatttgttc ctgtagataa taactaaggc    540
gcgcctttca ttttgttttt ttctatgcta taaatggtga gcaagggcga ggagctgttc    600
accgggtgg tgcccatcct ggtcgagctg gacggcgacg taaacggcca caagttcagc     660
gtgtccggcg agggcgaggg cgatgccacc tacggcaagc tgaccctgaa gttcatctgc    720
accaccggca agctgcccgt gccctggccc accctcgtga ccaccctgac ctacggcgtg    780
cagtgcttca gccgctaccc cgaccacatg aagcagcacg acttcttcaa gtccgccatg    840
cccgaaggct acgtccagga gcgcaccatc ttcttcaagg acgacggcaa ctacaagacc    900
cgcgccgagg tgaagttcga gggcgacacc ctggtgaacc gcatcgagct gaagggcatc    960
gacttcaagg aggacggcaa catcctgggg cacaagctgg agtacaacta caacagccac   1020
aacgtctata tcatggccga caagcagaag aacggcatca aggtgaactt caagatccgc   1080
cacaacatcg aggacggcag cgtgcagctc gccgaccact accagcagaa cacccccatc   1140
ggcgacggcc ccgtgctgct gcccgacaac cactacctga gcacccagtc cgccctgagc   1200
aaagacccca acgagaagcg cgatcacatg gtcctgctgg agttcgtgac cgccgccggg   1260
atcactctcg gcatgcacga gctgtacaag taagagctcg aggacgggag aattaactag   1320
tattgtacaa gaagccattt tatctctaaa tttacgaatt aagattttaa attttaaaca   1380
taaagatgat gatacgtata tacacttttg taaaatattt ttcggtgtct ataacggaac   1440
aaacgctact atatattatc atagacctct aacgggatat atgaatatga tttcagatac   1500
tatatttgtt cctgtagata ataactaact cgaggccgct ggtacccaac ctaaaaattg   1560
aaaataaata caaaggttct tgagggttgt gttaaattga agcgagaaa taatcataaa    1620
taagcccggg atgatgagga agctagcgat cctatccgtg tcgtccttcc tattcgtcga   1680
ggcgctattc caagagtacc agtgctatgg atcctcgtct aacaccagga tcctcaacga   1740
gctgaactac gacaacgctg gaacgaacct atacaacgag ctagagatga actactacgg   1800
caagcaagag aactggtaca gtctcaagaa gaactccaga tccctcggag agaacgacga   1860
tggcaacaac gaggacaacg agaagctaag gaagccgaac cacaagaacc tgaagcaacc   1920
ggctgatggg aatccagatc caggtggtgg atccaacaag aacaatcaag caacggaca    1980
aggacacaac atgccgaatg atccgaatag aacgtagac gagaacgcga acgcgaactc    2040
tgccgtgaag aacaacaaca acgaagaacc gtccgacaag cacatcaagg agtacctcaa   2100
caagtccag aactctctat ccaccgaatg gtctccatgt tctgtaacat gtggaaacgg    2160
aatccaagtc agaatcaagc caggatctgc gaacaagccg aaggatgaac tagattacgc   2220
gaacgacatc gagaagaaga tctgcaagat ggagaagtgc tcctccgtgt tcaacgtcgt   2280
caattcttaa taatttttat gtcgacctgc agtcaaactc taatgaccac atctttttt    2340
agagatgaaa aattttccac atctcctttt gtagacacga ctaaacattt tgcagaaaaa   2400
agtttattag tgtttagata atcgtatact tcatcagtgt agatagtaaa tgtgaacaga   2460
taaaaggtat tcttgctcaa tagattggta aattccatag aatatattaa tccttttcttc   2520
ttgagatccc acatcatttc aaccagagac gttttatcca atgatttacc tcgtactata   2580
ccacatacaa aactagattt tgcagtgacg tcgtatctgg tattcctacc aaacaaaatt   2640
ttacttttag ttcttttaga aaattctaag gtagaatctc tatttgccaa tatgtcatct   2700
atggaattac cactagcaaa aaatgataga aatatatatt gatacatcgc agctggtttt   2760
gatctactat acttttaaaaa cgaatcagat tccataattg cctgtatatc atcagctgaa   2820
aaactatgtt ttacacgtat tccttcggca tttcttttta atgatatatc ttgtttagac   2880
aatgataaag ttatcatgtc catgagagac gcgtctccgt atcgtataaa tatttcatta   2940
gatgttagac gcttcattag gggtatactt ctataaggcg tcttaatcag tccatcattg   3000
gttgcgtcaa gaacaagctt gtctccctat agtgagtcgt attagagctt ggcgtaatca   3060
tggtcatagc tgtttcctgt gtgaaattgt tatccgctca caattccaca acatacga     3120
gccgaagca taaagtgtaa agcctggggt gcctaatgag tgagctaact cacattaatt   3180
gcgttgcgct cactgcccgc tttcgagtcg ggaaacctgt cgtgccagct gcattaatga   3240
atcggccaac gcgcggggag aggcggtttg cgtattgggc gctcttccgc ttcctcgctc   3300
actgactcgc tgcgctcggt cgttcggctg cggcgagcgg tatcagctca ctcaaaggcg   3360
gtaatacggt tatccacaga atcagggat aacgcaggaa agaacatgtg agcaaaaggc    3420
cagcaaaagg ccaggaaccg taaaaaggcc gcgttgctgg cgtttttcga taggctccgc   3480
cccccctgacg agcatcacaa aaatcgacgc tcaagtcaga ggtggcgaaa cccgacagga   3540
ctataaagat accaggcgtt tccccctgga agctccctcg tgcgctctcc tgttccgacc   3600
```

```
ctgccgctta ccggatacct gtccgccttt ctcccttcgg gaagcgtggc gctttctcat 3660
agctcacgct gtaggtatct cagttcggtg taggtcgttc gctccaagct gggctgtgtg 3720
cacgaacccc ccgttcagcc cgaccgctgc gccttatccg gtaactatcg tcttgagtcc 3780
aacccggtaa gacacgactt atcgccactg gcagcagcca ctggtaacag gattagcaga 3840
gcgaggtatg taggcggtgc tacagagttc ttgaagtggt ggcctaacta cggctacact 3900
agaaggacag tatttggtat ctgccgctctg ctgaagccag ttaccttcgg aaaaagagtt 3960
ggtagctctt gatccggcaa acaaaccacc gctggtagcg gtggtttttt tgtttgcaag 4020
cagcagatta cgcgcagaaa aaaaggatct caagaagatc ctttgatctt ttctacgggg 4080
tctgacgctc agtggaacga aaactcacgt taagggattt tggtcatgag attatcaaaa 4140
aggatcttca cctagatcct tttaaattaa aaatgaagtt ttaaatcaat ctaaagtata 4200
tatgagtaaa cttggtctga cagttaccaa tgcttaatca gtgaggcacc tatctcagcg 4260
atctgtctat ttcgttcatc catagttgcc tgactcccg tcgtgtagat aactacgata 4320
cgggagggct taccatctgg ccccagtgct gcaatgatac cgcgagaccc acgctcaccg 4380
gctccagatt tatcagcaat aaaccagcca gccggaaggg ccgagcgcag aagtggtcct 4440
gcaactttat ccgcctccat ccagtctatt aattgttgcc gggaagctag agtaagtagt 4500
tcgccagtta atagtttgcg caacgttgtt ggcattgcta caggcatcgt ggtgtcacgc 4560
tcgtcgtttg gtatggcttc attcagctcc ggttcccaac gatcaaggcg agttacatga 4620
tcccccatgt tgtgcaaaaa agcggttagc tccttcggtc ctccgatcgt tgtcagaagt 4680
aagttggccg cagtgttatc actcatggtt atggcagcac tgcataattc tcttactgtc 4740
atgccatccg taagatgctt ttctgtgact ggtgagtact caaccaagtc attctgagaa 4800
tagtgtatgc ggcgaccgag ttgctcttgc ccggcgtcaa tacgggataa taccgcgcca 4860
catagcagaa ctttaaaagt gctcatcatt ggaaaacgtt cttcggggcg aaaactctca 4920
aggatcttac cgctgttgag atccagttcg atgtaaccca ctcgtgcacc caactgatct 4980
tcagcatctt ttactttcac cagcgtttct gggtgagcaa aaacaggaag gcaaaatgcc 5040
gcaaaaaagg gaataagggc gacacggaaa tgttgaatac tcatactctt ccttttcaa 5100
tattattgaa gcatttatca gggttattgt ctcatgagcg gatacatatt tgaatgtatt 5160
tagaaaaata aacaaatagg ggttccgcgc acatttcccc gaaaagtgcc acctgacgtc 5220
taagaaacca ttattatcat gacattaacc tataaaaata ggcgtatcac gaggccctt 5280
cgtctcgcgc gtttcggtga tgacggtgaa aacctctgac acatgcagct cccggagacg 5340
gtcacagctt gtctgtaagc ggatgccggg agcagacaag cccgtcaggg cgcgtcaggg 5400
ggtgttggcg ggtgtcgggg ctggcttaac tatgcggcat cagagcagat tgtactgaga 5460
gtgcaccata tgcggtgtga aataccgcac agatgcgtaa ggagaaaata ccgcatcagg 5520
cgccattcgc cattcaggct gcgcaactgt tgggaagggc gatcggtgcg ggcctcttcg 5580
ctattacgcc agctggcgaa aggggggatgt gctgcaaggc gattaagttg ggtaacgcca 5640
gggtttccc agtcacgacg ttgtaaaacg acggccagtg aattggattt aggtgacact 5700
ata                                                                5703
```